US010271750B2

(12) United States Patent
Maden et al.

(10) Patent No.: US 10,271,750 B2
(45) Date of Patent: Apr. 30, 2019

(54) SYSTEM AND METHOD FOR ASSESSING PERFUSION IN AN ANATOMICAL STRUCTURE

(71) Applicant: Perfusion Tech IVS, Copenhagen Ø (DK)

(72) Inventors: Mads Holst Aagaard Maden, Copenhagen Ø (DK); Morten Toft Lund, Copenhagen N (DK)

(73) Assignee: PERFUSION TECH IVS, Copenhagen Ø (DK)

( * ) Notice: Subject to any disclaimer, the term of this patent is extended or adjusted under 35 U.S.C. 154(b) by 0 days.

(21) Appl. No.: 15/838,071

(22) Filed: Dec. 11, 2017

(65) Prior Publication Data

US 2018/0160916 A1   Jun. 14, 2018

(30) Foreign Application Priority Data

Dec. 9, 2016 (EP) .................................... 16203188

(51) Int. Cl.
*A61B 5/0275* (2006.01)
*A61B 5/026* (2006.01)
(Continued)

(52) U.S. Cl.
CPC .......... *A61B 5/0275* (2013.01); *A61B 5/0071* (2013.01); *A61B 5/0261* (2013.01);
(Continued)

(58) Field of Classification Search
CPC .................................................. A61B 5/0275
See application file for complete search history.

(56) References Cited

U.S. PATENT DOCUMENTS 8,976,481 B1 *  3/2015  Zeng .................... G11B 5/6076
                                                        360/48
9,610,021 B2 *  4/2017  Dvorsky .............. A61B 5/0275
(Continued)

FOREIGN PATENT DOCUMENTS

WO       2009092162 A1     7/2009

OTHER PUBLICATIONS

Liu, J. et al. A Stable Optic-Flow Based Method for Tracking Colonoscopy Images, 2008 IEEE Computer Society Conference on Computer Vision and Pattern Recognition Workshops, Jun. 23-28, 2008, Anchorage, AK, USA, IEEE, 2008.
(Continued)

*Primary Examiner* — Rochelle D Turchen
(74) *Attorney, Agent, or Firm* — Dinsmore & Shohl, LLP

(57) ABSTRACT

A system is provided for measuring and assessing hemodynamics in an anatomical structure of a subject, along with a method for image processing hemodynamics in at least a part of an anatomical structure in video images acquired from a subject. The system and method relates to measuring and assessing hemodynamics in, around and near the surface, in particular the gastrointestinal wall, of the gastrointestinal tract of a subject. A method for image processing hemodynamics in at least a part of an anatomical structure in video images acquired from a subject may performing image analysis of at least one video sequence acquired after a fluorescent contrast agent has been supplied to the subject, calculating intensity values in one or more regions of interest based on the image analysis, and determining the perfusion slope of the flow of the fluorescent contrast agent through at least one of said regions of interest.

21 Claims, 11 Drawing Sheets

(51) Int. Cl.
*A61B 5/00* (2006.01)
*A61B 17/11* (2006.01)
*A61B 17/00* (2006.01)
*A61B 5/11* (2006.01)

(52) U.S. Cl.
CPC .......... *A61B 5/4255* (2013.01); *A61B 5/4552* (2013.01); *A61B 5/7225* (2013.01); *A61B 5/748* (2013.01); *A61B 17/1114* (2013.01); *A61B 5/0088* (2013.01); *A61B 5/1128* (2013.01); *A61B 5/4233* (2013.01); *A61B 5/4238* (2013.01); *A61B 5/4848* (2013.01); *A61B 5/7264* (2013.01); *A61B 2017/00818* (2013.01); *A61B 2576/00* (2013.01)

(56) References Cited

U.S. PATENT DOCUMENTS

| | | |
|---|---|---|
| 2010/0061604 A1 | 3/2010 | Nahm et al. |
| 2012/0155735 A1 | 6/2012 | Friedman et al. |
| 2014/0163403 A1 | 6/2014 | Lenox et al. |
| 2016/0262638 A1 | 9/2016 | Kamada et al. |
| 2017/0128059 A1* | 5/2017 | Coe .................. A61B 17/0218 |

OTHER PUBLICATIONS

Alander J. T. et al. A review of indocyanine green fluorescent imaging in surgery, International Journal of Biomedical Imaging, Hindawi Publishing Corporation, vol. 2012, Article ID 940585, 26 pages.

Boni, L., et al. Indocyanine green-enhanced fluorescence to assess bowel perfusion during laparoscopic colorectal resection, Surg Endosc (2016) 30:2736-2742.

Degett, T. H., et al. Indocyanine green fluorescence angiography for intraoperative assessment of gastrointestinal anastomotic perfusion: a systematic review of clinical trials, Langenbecks Arch Surg (2016) 401:767-775.

James, D. R. C., et al. Fluorescence angiography in laparoscopic low rectal and anorectal anastomoses with pinpoint perfusion imaging—a critical appraisal with specific focus on leak risk reduction, Colorectal Disease, 2015 The Association of Coloproctology of Great Britain and Ireland. 17 (Suppl. 3), 16-21.

Kudszus, S. et al. Intraoperative laser fluorescence angiography in colorectal surgery: a noninvasive analysis to reduce the rate of anastomotic leakage, Langenbecks Arch Surg (2010) 395:1025-1030.

Protyniak, B, et al. Intraoperative Indocyanine Green Fluorescence Angiography—An Objective Evaluation of Anastomotic Perfusion in Colorectal Surgery, Am. Surg. Jun. 2015;81(6):580-4.

Toens, C. et al: Validation of IC-VIEW fluorescence videography in a rabbit model of mesentereic ischaemia and reperfusion. Int J Colorectal Dis 2006;21:332-338.

Nerup, N. et al: Quantification of fluorescence angiography in a porcine model. Langenbecks Arch Surg, published online Jan. 15, 2016.

International Search Report for Application No. PCT/EP2017/082204, dated Apr. 4, 2018.

Extended EP Search Report for Application No. 16203188.4, dated Jun. 12, 2017.

* cited by examiner

SYSTEM AND METHOD FOR ASSESSING PERFUSION IN AN ANATOMICAL STRUCTURE

CROSS REFERENCE TO RELATED APPLICATIONS

This application claims priority from European Application No. 16203188.4 filed Dec. 9, 2016, the entire content of which is incorporated herein by reference.

BACKGROUND OF INVENTION

The present disclosure relates to a system for measuring and assessing hemodynamics in an anatomical structure of a subject, and a method for image processing hemodynamics in at least a part of an anatomical structure in video images acquired from a subject. In particular the present disclosure relates to measuring and assessing hemodynamics in, around and near the surface, in particular the gastrointestinal wall, of the gastrointestinal tract of a subject.

Complications related to the gastrointestinal tract are often related to local hemodynamics. I.e. a change in the normal hemodynamic conditions may be an indicator of a complication. Perfusion assessment of the gastrointestinal tract, in particular in and near the surface of the gastrointestinal tract, such as the tissue of the gastrointestinal wall, can therefore be an important diagnostic tool when examining the gastrointestinal tract, e.g. for diagnosis or for localization of a complication, for example during diagnostic laparoscopy, explorative laparoscopy or surgical laparoscopy with traditional laparoscopy or robotic surgery, as well as in open surgery. Perfusion assessment is also important during the surgical procedure of anastomosis which can be provided to establish communication between two formerly distant portions of the gastrointestinal tract. As an example intestinal anastomosis establishes communication between two formerly distant portions of the intestine and typically restores intestinal continuity after removal of a pathologic condition affecting the bowel. Intestinal anastomosis may for example be provided for 1) restoration of intestinal, such as bowel, continuity following resection of diseased intestine, and 2) bypass of unresectable diseased intestine, e.g. bowel. Certain pediatric conditions may also require intestinal anastomosis [6].

Resection of diseased bowel can be performed in the following settings:
  Bowel gangrene due to vascular compromise caused by mesenteric vascular disease, prolonged intestinal obstruction, intussusceptions, or volvulus
  Malignancy
  Benign conditions (e.g. intestinal polyps, intussusception, roundworm infestation with intestinal obstruction)
  Infections (e.g. tuberculosis complicated with stricture or perforation)
  Traumatic perforations
  Large perforations (traumatic) not amenable to primary closure
  Radiation enteritis complicated with bleeding, stricture, or perforation
  Inflammatory bowel disease, ulcerative colitis, or Crohn's disease that is refractory to medical therapy or associated with complications (e.g. bleeding, perforation, toxic megacolon, dysplasia/carcinoma)
  Chronic constipation, idiopathic slow transit constipation, or Hirschsprung's disease: Subtotal colectomy may be performed when the disease is refractory to medical therapy.

Bypass of unresectable diseased bowel can be performed in the following settings:
  Locally advanced tumor causing luminal obstruction
  Metastatic disease causing intestinal obstruction
  Poor general condition or condition that prevents major resection Pediatric conditions for which intestinal anastomosis may be required include the following:
  Congenital anomalies (e.g. Meckel diverticulum, intestinal atresia, malrotation with volvulus leading to gangrene, meconium ileus, duplication cysts, Hirschsprung's disease)
  Inflammatory conditions (e.g. necrotizing enteritis, enterocolitis, tuberculosis, enteric perforation)
  Other conditions (e.g. intussusception, angiodysplasia, polypoid disease, ascariasis)
  As a part of other surgical procedures (e.g. Kasai portoenterostomy, choledochal cyst, urinary diversions, pancreatic neoplasms)

Postsurgical complications in connection with anastomosis in the gastrointestinal tract are unfortunately frequent, often due to insufficient perfusion (capillary blood supply) at the anastomosis, i.e. the joining of the two parts of the tract. Insufficient perfusion may cause anastomotic leakage, which is a serious and frequent complication, for example in connection with colorectal surgery where more than 10% of the procedures result in complications. Within colon cancer surgery more than 30% of patients with anastomotic leakage die due to postoperative complications and approx. 25% of the remaining patients suffer from stoma for the rest of their lives. Risk factors associated with leakage include tension of anastomosis, tissue damage and in particular reduced blood perfusion.

SUMMARY OF INVENTION

A reliable procedure to assess perfusion in the gastrointestinal tract, in particular the wall of the gastrointestinal tract is therefore needed, more specifically before, during and after examination and/or surgery. In connection with bowel surgery where bowel resection, and possibly anastomosis, is needed a more reliable procedure is needed to reduce post-surgical complications. Today the surgeon is left with subjective parameters to assess perfusion, for example palpable pulse, color of tissue and active bleeding. Most advantageously the surgeon should be able to objectively quantify the perfusion intraoperatively such that decisions can be evaluated and revised during surgery. Assessment of the perfusion of, for example, an anastomosis would therefore be of great interest because it would allow the surgeon to intervene in appropriate situations, thereby possibly reducing the risk of leakage and prolonged hospital stay which increases the healthcare costs.

One solution could be the application of fluorescence imaging using a fluorescent dye injected in the blood of the patient. Fluorescence imaging in the form of Laser Fluorescence Angiography (LFA) has a proved correlation to perfusion [1]. However, an efficient utilization of fluorescence imaging requires signal processing in order to quantify the perfusion. It would be advantageous if tools were provided for the surgeon to objectively evaluate perfusion before, during and/or after surgery, for example before resection, before anastomosis and/or after anastomosis. The purpose of the present disclosure is therefore also to contribute to the improvement within diagnosis and treatment procedures of the gastrointestinal tract, in particular intestinal anastomosis, e.g. in connection with colorectal cancer treatment.

The present disclosure therefore in general relates to a system for measuring and assessing hemodynamics in the gastrointestinal tract of a subject, and a method for image processing hemodynamics in at least a part of the gastrointestinal tract in video images acquired from a subject.

A first embodiment comprises the steps of performing image analysis of at least one video sequence, preferably acquired after a fluorescent contrast agent has been supplied to the subject, preferably a bolus of the fluorescent contrast agent, and obtaining and/or calculating intensity values in one or more regions of interest in said video sequence(s) based on the image analysis.

A further embodiment relates to a method for image processing (mammalian) anastomosis hemodynamics (during an examining and/or surgical procedure involving the gastrointestinal tract) in video images acquired from a subject, comprising the steps of
performing image analysis of at least the following two video sequences, each video sequence acquired after a fluorescent contrast agent has been supplied to the subject:
 i. first video images representing a least a first part of the gastrointestinal tract, and
 ii. second video images representing at least a second part of the gastrointestinal tract, the second part of the gastrointestinal tract being different than the first part of the gastrointestinal tract,
calculating intensity values in one or more regions of interest based on the image analysis of the first video images and the second video images, and
determining the perfusion slopes of the flow of the fluorescent contrast agent through at least a first region of interest selected in the first video sequence and at least a second region of interest selected in the second video sequence.

Yet a further embodiment relates to a method for image processing (mammalian) anastomosis hemodynamics (during surgery involving the gastrointestinal tract) in video images acquired from a subject. The method preferably comprises the step of performing image analysis of one, two or more of the following video sequences, each video sequence acquired after a fluorescent contrast agent has been supplied to the subject:
 video images representing at least a part of the gastrointestinal tract acquired before resection,
 video images representing at least a part of the gastrointestinal tract acquired after resection but before anastomosis, and
 video images representing at least a part of the gastrointestinal tract acquired after anastomosis
Intensity values can then be calculated in one or more regions of interest based on the image analysis.

In general the present disclosure therefore relates to performing image analysis of one or more video sequences representing at least a part of the gastrointestinal tract, for example acquired before, during and/or after laparoscopy, in particular examining laparoscopy, diagnostic laparoscopy and/or surgical laparoscopy with traditional laparoscopy or robotic surgery, as well as in open surgery, involving the gastrointestinal tract. The intensity values obtained therefrom can be used to generate a number of chronological change curves, and the shape of said chronological change curve(s) can be analysed. From this analysis relative and/or quantitative data for perfusion, blood volume and/or blood flow can be determined, i.e. based on results of the image analysis of the video sequence(s). In particular the perfusion slope of the flow of the fluorescent contrast agent through at least one of the regions of interest can be determined.

A further embodiment of the present disclosure relates to a system for measuring and/or assessing hemodynamics in an anatomical structure of a subject, comprising an imaging device for acquiring video images of the exterior portion of at least a part of said anatomical structure, and an image processing device configured for carrying out any of the methods as disclosed herein.

The present disclosure further relates to a computer program having instructions which when executed by a computing device or system cause the computing device or system to measure and/or assess hemodynamics in an anatomical structure of a subject according to the described method. Computer program in this context shall be construed broadly and include e.g. programs to be run on a PC or software designed to run on an electronic medical device, such as an endoscope, or smartphones, tablet computers or other mobile devices.

The methods disclosed herein are advantageously computer implemented to provide for fast and reliable image processing and data analysis, possibly in real time or at least near real time such that they can be used intraoperative.

The presently disclosed method for obtaining a measure of hemodynamics may in a further embodiment contribute to an assessment of a patient's risk of postsurgical complications and thereby for example help the surgeon to make an informed choice of an appropriate follow-up program following examination or surgery personalized to each patient. One way to do this could be to combine the calculated perfusion parameter(s) with various relevant patient specific data such as age, gender, comorbidities, type of surgery etc. in a multivariate analysis, providing the surgeon with an automatically weighted risk score for each patient already during the surgery. Such an intelligent risk score can contribute to the surgeons' surgical decisions during any operation on the gastrointestinal tract, where a measurement of perfusion could be of interest.

By storing each patient's data from the multivariate analysis in an online database, preferably in fully anonymized form, this growing database can then be used to continuously update and refine the analysis itself. Resulting in an ever improving analysis and a decision support system based on each patient's personalized risk profile. I.e. what can be provided is a decision support system that aids the surgeon both during the operation to help reduce the risk of postsurgical complications, and after the operation when selecting the appropriate follow-up program.

BRIEF DESCRIPTION OF THE DRAWINGS

FIGS. 2B, 2D and 2F are close-ups of FIGS. 2A, 2C and 2E, respectively, where the slopes starts.

FIGS. 4B, 4D and 4F are close-ups of FIGS. 4A, 4C and 4E, respectively, where the curves have their maximum intensity.

FIGS. 5B, 5D and 5F are close-ups of FIGS. 5A, 5C and 5E, respectively, where the ICG is washed out.

DETAILED DESCRIPTION OF THE INVENTION

Figure 1A:
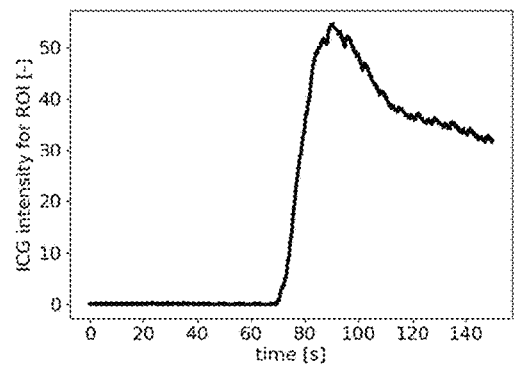
FIGS. 1A, 1C and 1E show examples of intensity curves after a bolus of ICG has been provided to a subject.

In general the present disclosure therefore relates to performing image analysis of one or more video sequences representing at least a part of the gastrointestinal tract, for example acquired before, during and/or after surgery, in particular surgery involving the gastrointestinal tract. This may in particular apply to gastrointestinal surgery—the video sequence may therefore comprise at an exterior portion of at least a part of the gastrointestinal tract, preferably such that perfusion in at least a part of the gastrointestinal wall can be measured and assessed.

The gastrointestinal tract is an organ system within humans and other animals which takes in food, digests it to extract and absorb energy and nutrients, and expels the remaining waste as feces and urine. The gastrointestinal tract can be seen as a tube that transfers food to the organs of digestion. The term gastrointestinal tract as used herein therefore includes the buccal cavity; pharynx; the small intestine including duodenum, jejunum, and ileum; the stomach, including esophagus, cardia, and pylorus; the large intestine including cecum, colon, rectum and the anal canal.

Image analysis can be provided to the whole image in each image of a video sequence. However, more relevant information can typically be extracted if one or more regions of interest (ROI) are selected in the images. At least a first of said regions of interest then preferably corresponding to a subsection of the gastrointestinal tract, i.e. at least one of said regions of interest may cover a section of an exterior portion of the gastrointestinal tract, i.e. such that perfusion in a section of the gastrointestinal wall can be assessed. However, advantageously at least one of said regions of interest may cover a section which is not gastrointestinal tract or at least not the same part of the gastrointestinal tract. E.g. if a surgery procedure is performed on the colon, the perfusion of the small intestine can be used as reference. This can be used for having a reference intensity measurement which is unaffected by the excitation light.

Video sequences as described herein can be acquired using natural light (visible to the human eye) or infrared light or a combination thereof. The input-format may for example be one channel of two superimposed images or two separate channels each containing a particular image-type. During surgery the natural light images may be shown to the surgeon before injection of the contrast agent. Once the contrast agent has been injected the fluorescent images are shown. However, data from both types of light sources may be acquired, combined, analysed and stored during the entire procedure. Tracking of movement may for example be easier in natural light images, e.g. if the tracked objects are not visible in infrared light. But the input video feed is often a 3D (e.g. RGB) matrix with an 'excess' of light-intensity in the green matrix dimension which can be the result of superimposing the two types of images.

Intraoperative Fluorescence Angiography

Blood flow can be imaged intra-operative and assessed in real time using the near-infrared light from a surgical microscope and acquiring video of fluorescent light in the near-infrared region that is excited from a fluorescent vascular contrast agent that has been intravenously administered as a tracer. The state of blood flow during the operation can thereby be confirmed in real-time.

During a diagnostic, screening, examining and/or surgical procedure involving fluorescence imaging a solvent comprising the fluorescent contrast agent, such as ICG, is injected intravenously and the molecules are excited by an infrared light source, e.g. a laser with a wavelength in the infrared wavelength range, e.g. around 780 nm. Fluorescent light with a wavelength of around 830 nm is then emitted from the excited contrast agent molecules and can be recorded with an imaging device, e.g. in the form of a camera. A filter can be provided to block the excitation light as the excitation intensity typically is much larger than the fluorescence intensity. The excitation intensity can be around 1 W per emission angle whereas the fluorescent power pr. pixel can be around 0.15 pW. In spite of the several orders of magnitude in difference, good Signal to Noise Ratio (SNR) can be achieved. The recorded fluorescent light provides an image of the perfusion in imaged tissue and makes it possible to see deeper lying blood vessels, due to a penetration depth of 5-10 mm for ICG. Since the ICG molecule is bound to proteins in the blood, the video images contain information about the level of perfusion—but that information can be difficult to quantify for the surgeon during the operation if only the acquired video images are seen.

In one embodiment of the present disclosure the fluorescent contrast agent is selected from the group of: indocyanin green (ICG) and fluorescein.

Perfusion Parameters

Various parameters can be determined based on image analysis and the extracted intensity values. The single most important parameter is the perfusion slope because it is a direct indication of the blood flow in the imaged tissue.

The configuration of the regions of interest, e.g. size of the regions, number of regions, locations in the image, etc., can be provided automatically, semi-automatically or manually by the user, e.g. the doctor/surgeon. With at least some kind of manual intervention the user may be able to select additional regions of interest or remove existing regions of interest. Preferably also move one or more of the regions around in the image such the regions of interest are located in relevant areas of the image, preferably prior to shooting of a video sequence.

The perfusion slope can be determined from the fluorescent intensity values integrated over a region of interest comprising tissue. Initially before injection of a contrast agent, the curve will be a substantially flat line. After the contrast agent has been injected the region of interest will begin to fluoresce as soon as a bolus of the contrast agent molecules have been excited and reach the region of interest—the result is a substantially linearly increasing line. When the bolus of contrast agent molecules levels off, so will the fluorescent intensity in the region of interest and washout will begin where the amount of contrast agent molecules decrease (substantially linear) to zero.

But this is the idealized scenario and the curves can vary from time to time and from patient to patient and it is therefore important with robust definitions of the perfusion parameters such that they can be determined automatically on the fly to be repeatable and comparable.

The perfusion slope can be defined by the slope of the extracted intensity values from slope start to slope end. The perfusion slope can merely be determined as a linear fit to the curve. The challenge is to determine the start point (slope start) and the end point of the fit (slope end), in particularly in a real time situation. Slope start is the most important of the two and can be defined as the point in time where the slope exceeds a predefined first threshold. The first threshold can for example be determined by three parameters: a predefined factor k, and the mean and standard deviation (std) of intensity values prior to slope start or prior to supply of the fluorescent contrast agent. Slope start can then be defined as the time point where the slope exceeds the mean by k*std. Slope end can correspondingly be defined as the point in time, after slope start, where the slope is reduced by more than a predefined second threshold. The constant k can be determined based on the setup, but typically k will be in the range of 3-10.

However, advantageously the perfusion slope can be determined from a histogram in a parameter space binning all slopes after slope start and where the perfusion slope is determined as the most frequent value of the histogram. I.e. after slope start a slope value is calculated for all subsequent intensity points based on slope start. Slope end can then be deduced therefrom. The slope values calculated immediately after slope start can be assigned more weight in the histogram than later slope values because it is certain that the perfusion slope has initiated after slope start. E.g. the first 100 calculated slope values can be assigned weights of 100, 99, 98, . . . etc., respectively, in the histogram. If a higher constant k is selected, the initial values of the perfusion slope can be assigned even more weight. The histogram centred approach is very precise and can advantageously be used in a real-time or near-real-time situation.

Another parameter that can be determined is the washout slope which is an indication of the extinctive flow of the contrast agent, e.g. through at least one of said regions of interest. Whereas the perfusion slope typically is positive due to the increasing flow of the contrast agent, the washout slope is opposite (in sign) to the perfusion slope, i.e. typically negative. The washout slope can add information about the perfusion in the tissue. However, the washout slope may also be relevant as an indication of the function of organs such as the liver. Similar to the perfusion slope, the washout slope can be defined by the slope of said intensity values from washout start to washout end. Washout start occurs after slope end. The washout slope can be determined from a histogram in a parameter space binning all slopes after washout start and where the washout slope is determined as the most frequent value of the histogram. As described above for the perfusion slope, some of the calculated washout slope values may be assigned more weight in the histogram than others, in particular the initial values of the washout slope after washout slope start.

The max intensity reached can easily be determined, e.g. for each ROI. However, a more relevant parameter could be the max slope intensity which is the intensity where the intensity values begin to level off. The max slope intensity can be defined as the intensity value at slope end. A more precise definition could be the intensity value at the time point where the distance to the straight line, which has the perfusion slope as gradient and intersects the curve-point determined by slope start, exceeds a predefined limit, for example a limit based on e.g. the standard deviation of the perfusion slope. E.g. the max slope intensity can be where the intensity level differs from the perfusion slope by a predefined factor times the standard deviation of the perfusion slope.

The slope rise time might also be relevant and can be defined as the difference between the time point of the max slope intensity and slope start, i.e. for how long does the contrast agent take to flow through, or accumulate in, the tissue, which can be an indication of the speed of the blood flow.

The relative perfusion slope can then be defined as the inverse of the slope rise time. A subject specific relative perfusion slope can then be defined as the relative perfusion slope times the maximum intensity of a region of interest where perfusion is at a local (or global) extrema. I.e. a perfusion parameter which is normalized to become a patient specific perfusion slope parameter.

Tracking

In a further embodiment tracking of movement of the gastrointestinal tract in said video images is provided. This tracked movement of the gastrointestinal tract can be used such that at least said first region of interest corresponds to the same subsection of the gastrointestinal tract in said video images.

The purpose of tracking is primarily to ensure that the data, e.g. pixel intensity values, is sampled from the same tissue-area. Thus, if the gastrointestinal tract moves in the image, tracking should ensure that any regions of interest as defined herein would correspondingly move to ensure that the sampled data for said regions of interest is intelligible. In that regard is does not matter whether it is the gastrointestinal tract that physically moves, e.g. due to subject respiration and/or peristaltic movements, or it is the imaging device acquiring the images that moves relative to the gastrointestinal tract. What matters is whether the imaged object moves inside the acquired images.

A further aspect of the present disclosure therefore relates more generally to a (computer implemented) method for image processing movements/dynamics of at least a part of the gastrointestinal tract (e.g. during examination or surgery) from video images representing at least an exterior portion of said gastrointestinal tract, comprising the steps of:
selecting one or more regions of interest in at least one of said video images, at least a first of said regions of interest corresponding to a subsection of the gastrointestinal tract,
tracking movement of the gastrointestinal tract in said video images, and
correlating said movement of the gastrointestinal tract such that at least said first region of interest corresponds to the same subsection of the gastrointestinal tract in said video images.

Tracking of objects in a sequence of images, such as a video sequence, can be provided in different ways. Roughly speaking there are at least two different approaches: Free Image Tracking (FIT), which is based on the input video feed only, and Object Based Tracking (OBT), wherein predefined and/or recognizable objects are attached to the object that is being tracked in the images.

Free image tracking can for example be provided by means of classifiers: based on the input image a classifier algorithm computes classifiers of the most recognizable features in the area surrounding a given ROI (for more ROIs each ROI will be assigned a sensitivity-region within which the tracking works for the given ROI). In one embodiment of the present disclosure gastrointestinal tract movement tracking is provided by free image tracking, for example in the form of classifier based tracking comprising the step of determining classifiers of one more recognizable features in the video images, preferably in an area adjacent or surrounding at least one of the regions of interest.

Free image tracking can also be based on color based tracking: prior to the procedure, such as surgery, minimum one ROI of the object, such as the bowel, have been marked with a color and/or tattoo, preferably a predefined color or tattoo. The marking can be provided by for example the surgeon. If it is the actual ROIs that have been marked, a color based algorithm can obtain the form of the marking and use this form as the specific region of interest. A color based algorithm can be configured to initially perform a color filtering and subsequently object identification. Based on the properties of the marker (primarily the color) a target RGB- or HSV-index can be provided for the filtering. A filtering, for example in the form of a HSV-thresholding, can then be provided to obtain a Boolean map of the input image pixels and this Boolean map will only contain pixels covering the marker. The object identification can then be provided by for example a noise-filtering, such as by opening or closing based on Erosion/Dilation, in order to remove noise from the Boolean map. With these noise-filter(s) an improved Boolean map can be obtained with "filled" ROIs. I.e. the resulting Boolean map will be full of zeroes except for patches filled with ones (or vice versa) and each patch will correspond to a ROI.

In object based tracking one or more objects are physically attached to the target that must be tracked, e.g. the bowel. As the object(s) are typically predefined in terms of for example size, shape and color, classifiers can be trained prior to the tracking, i.e. the tracking system used can be configured to automatically recognize (and thereby track) the predefined objects. In one embodiment of the present disclosure gastrointestinal tract movement tracking is provided by object based tracking, such as by tracking the movement of one or more predefined objects attached to the gastrointestinal tract.

As an example of object based tracking two (or more) spheres (or another geometrically well-defined object) can be attached to a 'top' part of the gastrointestinal tract and one (or more) sphere on the lower/bottom part of the gastrointestinal tract (seen from the imaging device). If the objects attached to the top part are different from the object(s) attached to the bottom part it will be easy to distinguish the top part from the bottom part. If the spheres emit a tracker they are furthermore easily recognizable and therefore easily trackable. They could for example contain a fluorescent agent such that the spheres are visible when excited. They can then be identified in the images by for example a Hough-circle-recognition (or another feature-extraction). They can also be colored and identified by the color recognition method described above. Since the 'top'/'bottom' object are predefined and therefore known beforehand it is easy to train classifiers for both types of objects. To train a classifier for an object a large database of pictures of said object can be used to train a classifier. The position of the 'top' and 'bottom' objects in the images can thereby be determined very precisely by using classifiers.

As the objects are fixed to the target, e.g. the tissue of the bowel, ROI's can be defined based on these objects (e.g. 'top' and 'bottom'). For example in the case when using four objects, the ROI corners could simply correspond to the four tracked object positions. In case of two objects a ROI could be defined between the two object-positions: e.g. a parallelogram which expands in the middle to half height—this determines the angles.

Perfusion Assessment

Much valuable information can be provided from the perfusion parameters mentioned above. However, in order to qualify the perfusion parameters some kind of reference might be necessary.

In one embodiment video sequences acquired from different parts of the gastrointestinal tract can be used to calculate perfusion parameters relating to each part and these perfusion parameters can be compared such that the perfusion in the different parts of the gastrointestinal tract can be compared, i.e. the perfusion parameters obtained from one of the video sequences can be used as reference such that a quantitative assessment of the perfusion can be provided between the video sequences relating to different parts of the gastrointestinal tract.

In another embodiment different regions of interest from the same video sequence can be selected such that the perfusion parameters relating to one of the regions of interest is used as a reference for the other regions of interest such that a quantitative assessment of the perfusion can be provided between the different regions of interest in the same video sequence.

A further embodiment therefore further comprising the steps of:
performing image analysis of at least the following two video sequences, each video sequence acquired after a fluorescent contrast agent has been supplied to the subject:
first video images representing at least a first part of the gastrointestinal tract, and
second video images representing at least a second part of the gastrointestinal tract, the second part of the gastrointestinal tract being different than the first part of the gastrointestinal tract, calculating intensity values in one or more regions of interest based on the image analysis of the first video images and the second video images, and determining the perfusion slopes of the flow of the fluorescent contrast agent through at least a first region of interest selected in the first video sequence and at least a second region of interest selected in the second video sequence.

A further embodiment more specifically relates to the anastomosis process where perfusion assessment can be an important indication of where to provide the resection and whether the final anastomosis has sufficient perfusion. A further embodiment therefore further comprises the steps of:

performing image analysis of two or more of the following video sequences, each video sequence acquired after a fluorescent contrast agent has been supplied to the subject:

a) video images acquired before intestinal resection, such as bowel resection, b) video images acquired after resection but before anastomosis, and c) bowel video images acquired after anastomosis.

calculating intensity values in one or more regions of interest based on the image analysis, wherein at least a first of said regions of interest is the same region in said two or more video sequences, and determining the perfusion slopes of the flow of the fluorescent contrast agent through at least the first region of interest based on said two or more video sequences.

Based on these two or more video sequences one or more of the following parameters can be determined based on said two or more video sequences: the washout slopes, the max slope intensities, the relative perfusion slopes and the subject specific relative perfusion slopes.

Having parameters from two (or more) video sequences acquired at different times during the surgery makes it possible to use the parameter(s) extracted from one video sequence as reference parameter(s). Hence, quantitative data for the perfusion in at least one of said regions of interest based on slope parameters can be determined from said at least two video sequences. The result is that quantitative and qualitative evaluation parameters can be provided to the surgeon during and after gastric surgery, for example assisting in evaluation if an intestinal, e.g. bowel, resection looks promising and after surgery the result can be evaluated almost instantly, e.g. assessing whether an anastomosis has sufficient perfusion, for example by comparing perfusion parameters obtained before and after the surgery it is possible to quantify how much the perfusion dropped. In that case tracking of intestinal, e.g. bowel, movements can be key because tracking is one way to ensure that it is the same regions of interest that are assessed regarding perfusion before and after surgery.

Thresholds can be provided which are specific to the perfusion parameters. Also an uncertainty can be associated with a given threshold. A threshold comparison can for example indicate whether the operation went well or if the perfusion according to the parameter(s) in question has dropped below a critical level. And for several perfusion parameters a "weighted average answer" can also be provided.

In one embodiment of the present disclosure the perfusion slope (and/or other perfusion parameters as described) is calculated from video sequences acquired before resection and acquired after resection but before anastomosis. The relationship between the two perfusion slopes is a measure of the difference in perfusion before and after resection. If the perfusion drops below a predefined threshold after resection a warning can be given. More information can be extracted if perfusion slopes are calculated before and after resection for two, three or more regions of interest—and these regions of interest are the same tissue regions imaged before and after resection.

EXAMPLES

Figure 1B:
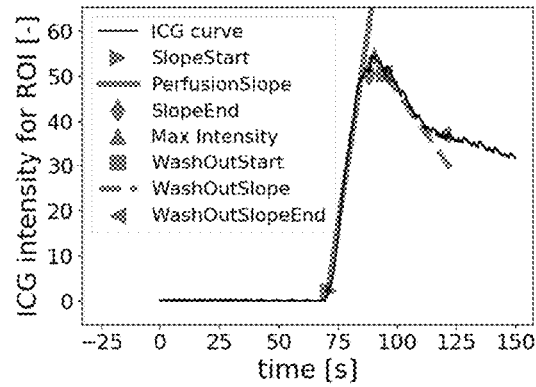
FIGS. 1B, 1D, and 1F show the corresponding intensity curves where the hemodynamic parameters perfusion slope, slope start, slope end max intensity, washout slope, washout start and washout slope end have been calculated and are indicated in the graphs.
Figure 1C:
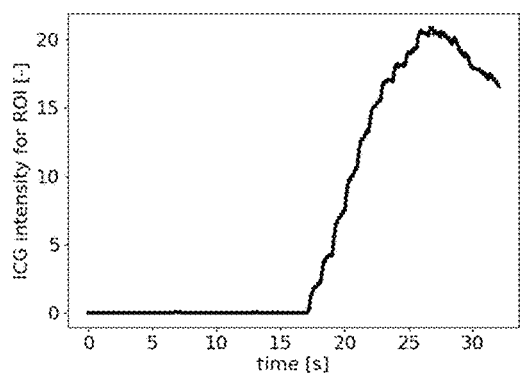
Figure 1D:
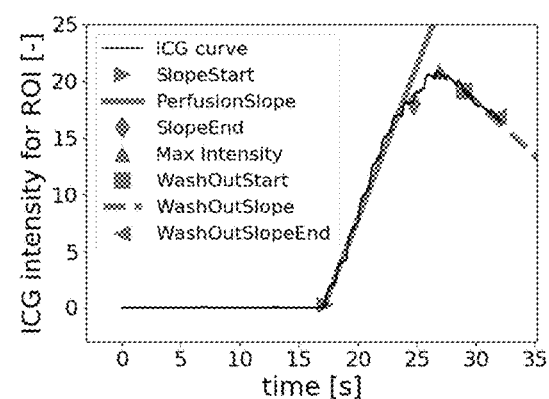
Figure 1E:
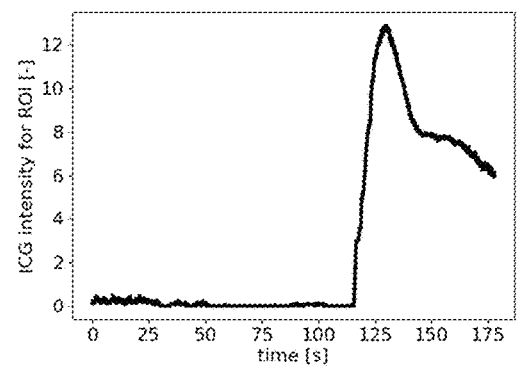
Figure 1F:
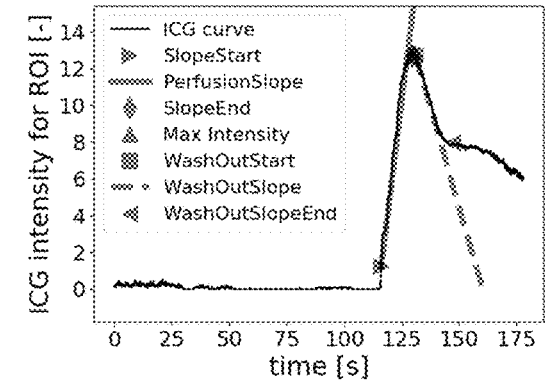

FIGS. 1A, 1C and 1E show examples of intensity curves acquired from tissue after a bolus of ICG has been provided to a subject, e.g. from a region of interest in a video sequence. The same kind of data could be obtained if another contrast agent was used. The intensity is substantially zero until a steep rise in intensity indicates the passage of ICG molecules in the imaged tissue, the ICG molecules being excited to fluoresce. The peak in intensity is followed by the gradual washout of the ICG molecules. The intensity is indicated with arbitrary units. FIGS. 1B, 1D, and 1F show the corresponding intensity curves where the hemodynamic parameters perfusion slope, slope start, slope end max intensity, washout slope, washout start and washout end have been calculated and are indicated in the graphs.

Figure 2A:
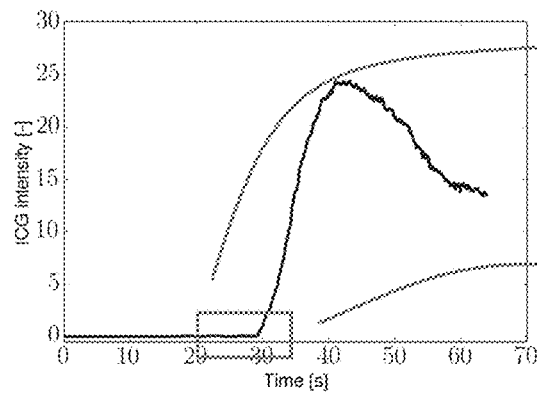
FIGS. 2A-2F show three examples illustrating the herein disclosed approach of determining the point in time where the perfusion slope starts, i.e. slope start.
Figure 2B:
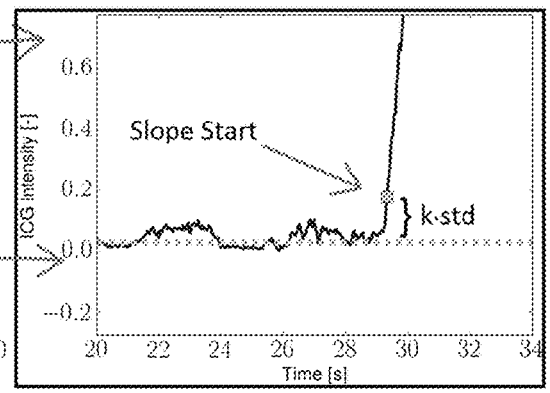
Figure 2C:
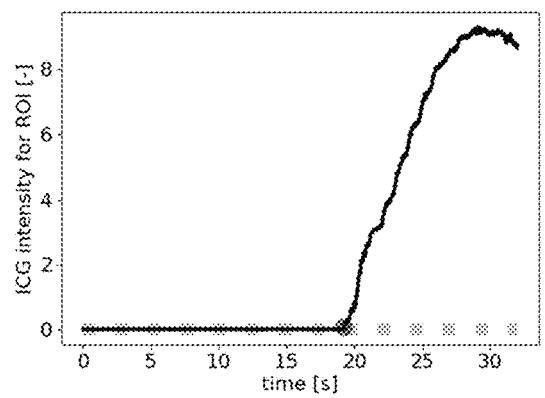
Figure 2D:
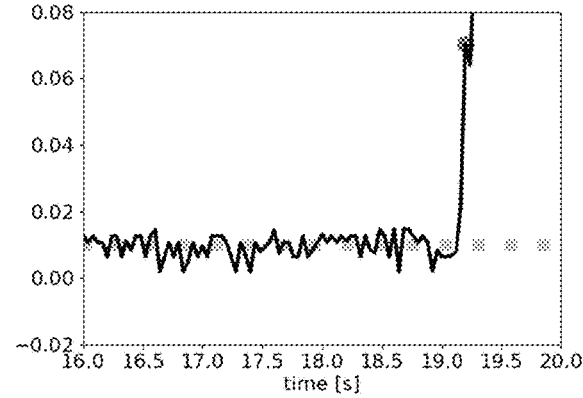
Figure 2E:
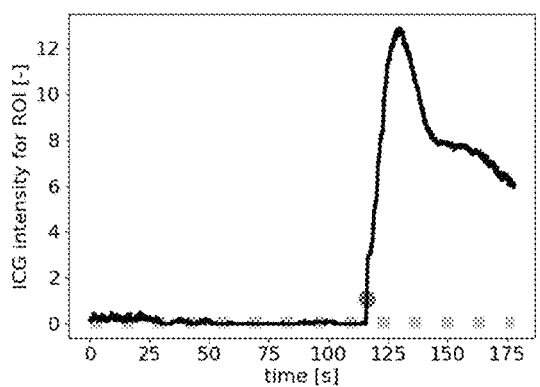
Figure 2F:
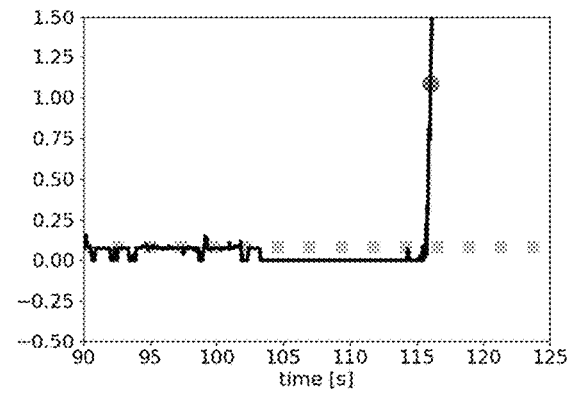
Figure 3A:
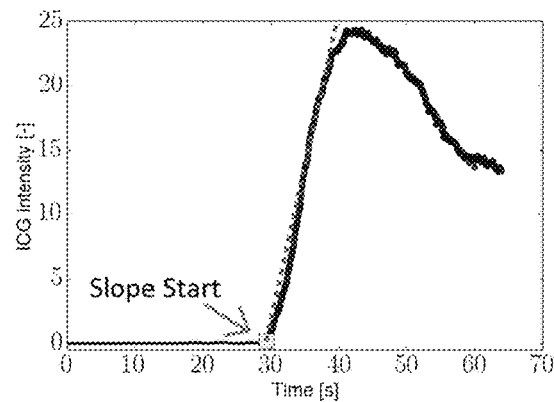
FIGS. 3A-3F show three examples illustrating the herein disclosed approach of determining the perfusion slope based on histogram data.
Figure 3B:
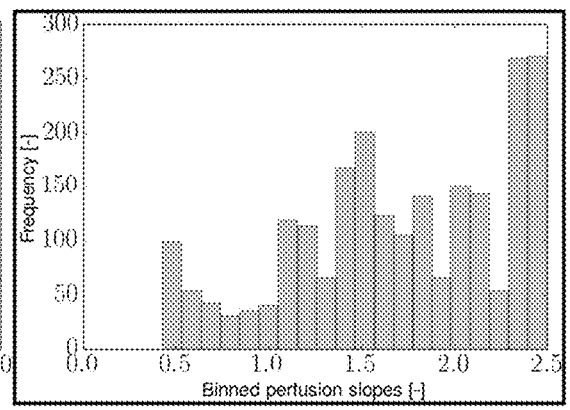
Figure 3C:
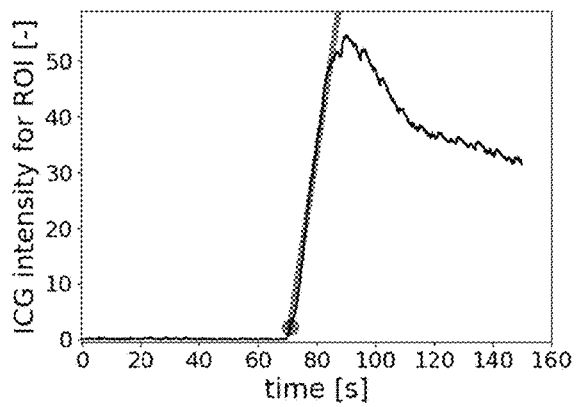
Figure 3D:
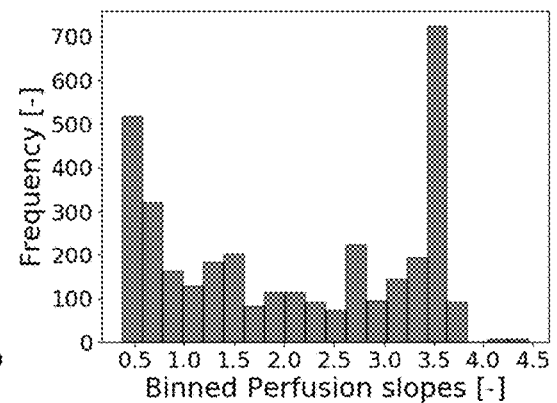
Figure 3E:
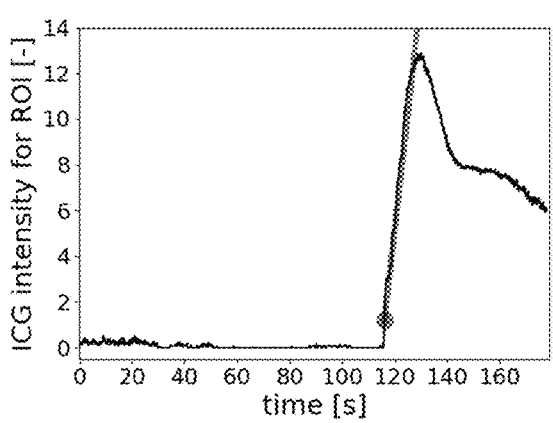
Figure 3F:
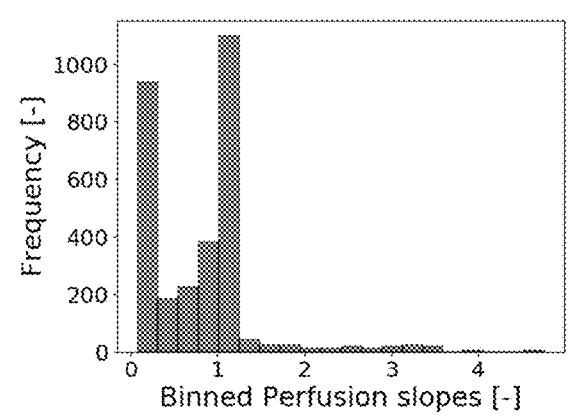

FIGS. 2A-2F show three examples illustrating the herein disclosed approach of determining the point in time where the perfusion slope starts, i.e. slope start. FIGS. 2B, 2D and 2F are close-ups of FIGS. 2A, 2C and 2E, respectively, where the slopes starts, i.e. the graphs to the right show a close-up of the curve to the left where the slope start is more detailed. Slope start is seen to be defined as the time point where the slope exceeds the mean by k*std, where k is a predefined constant and std is the standard deviation of intensity values prior to slope start. The slope start is indicated as a circle in FIG. 2B.

FIGS. 3A-3F show three examples illustrating the herein disclosed approach of determining the perfusion slope based on histogram data. The graphs to the left shows intensity curves, where FIG. 3A corresponds to FIG. 2A and FIG. 3E corresponds to FIG. 2E. The slope starts are indicated, by an arrow in FIG. 3A and by circles in FIGS. 3C and 3E. From slope start and to the end of the intensity curve all possible slopes of the intensity curve have been calculated. All the calculated slopes are collected and binned in the histograms shown to the right. The perfusion slopes are defined as the most frequent value of the histograms, i.e. the highest histogram bin. The calculated perfusion slopes of each of the intensity curves in FIGS. 3A, 3C and 3E, i.e. the highest histogram bin in FIGS. 3B, 3D, and 3F, respectively, are marked by straight lines in FIGS. 3A, 3C and 3E.

Figure 4A:
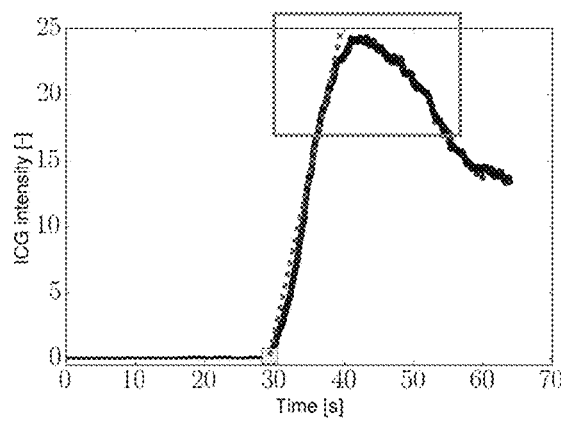
FIGS. 4A-4F show three examples illustrating the herein disclosed approach of defining and determining the max slope intensity.
Figure 4B:
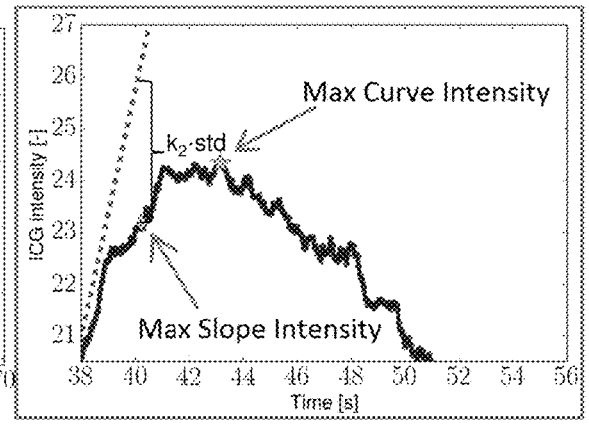
Figure 4C:
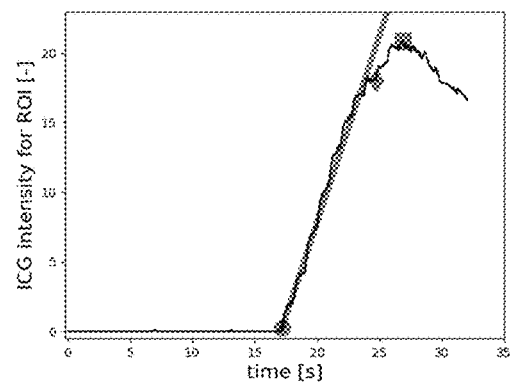
Figure 4D:
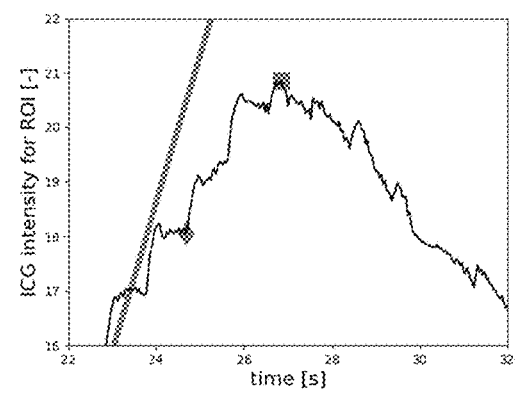
Figure 4E:
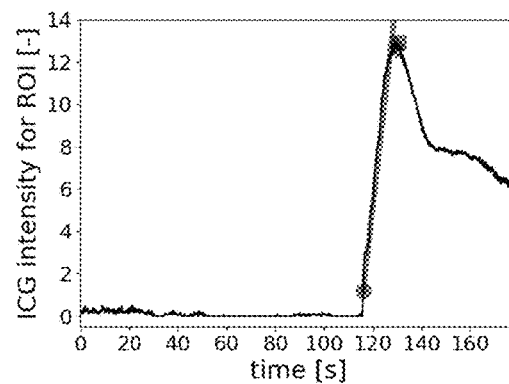
Figure 4F:
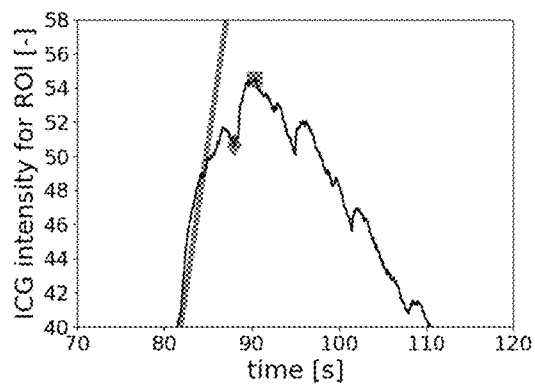

FIGS. 4A-4F show three examples illustrating the herein disclosed approach of defining and determining the max slope intensity. FIGS. 4B, 4D and 4F are close-ups of FIGS. 4A, 4C and 4E, respectively, where the curves have their maximum intensity. The maximum intensity of the curve is indicated by a star in FIG. 4B and by a square in FIGS. 4D and 4F along with the max slope intensity, which is indicated as a diamond in the figures. The max slope intensity is defined as the intensity value at the time point where the distance to the perfusion slope exceeds a predefined limit, for example a limit based on constant ($k_2$) times the standard deviation of the perfusion slope. As seen in FIG. 4 there can be significant differences in time and intensity between the maximum intensity of the curve and the max slope intensity. The slope rise time can be defined as the difference between peak (maximum) intensity of the curve and slope start. But as illustrated here the slope rise time defined as the difference between max slope intensity and slope start gives a more relevant definition of the slope rise time.

Figure 5A:
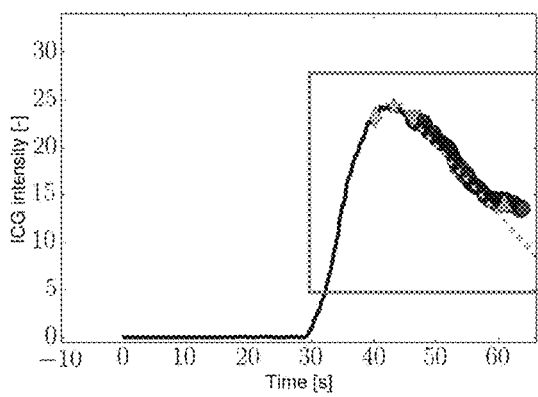
FIGS. 5A-5F show three examples illustrating the herein disclosed approach of analysing the washout of the fluorescence contrast agent.
Figure 5B:
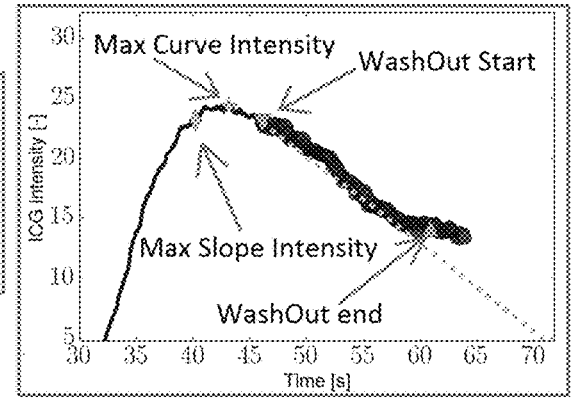
Figure 5C:
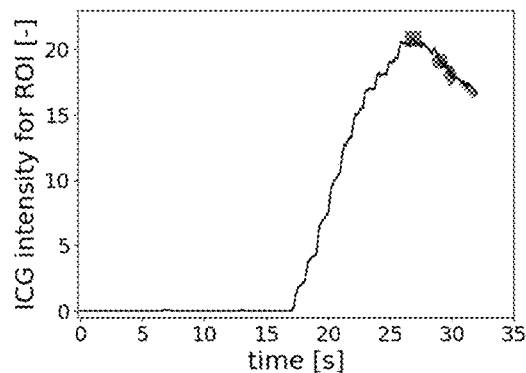
Figure 5D:
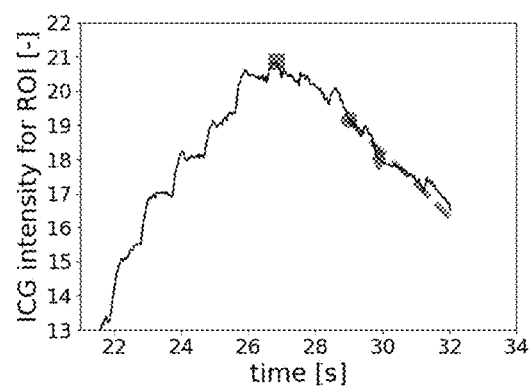
Figure 5E:
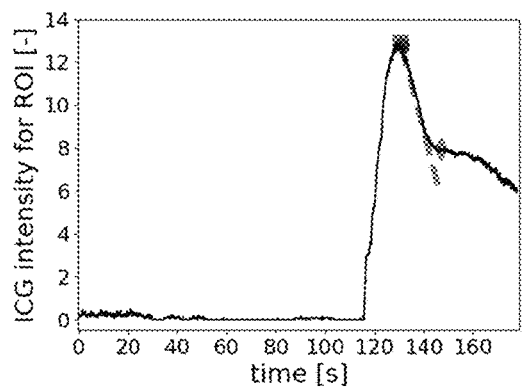
Figure 5F:
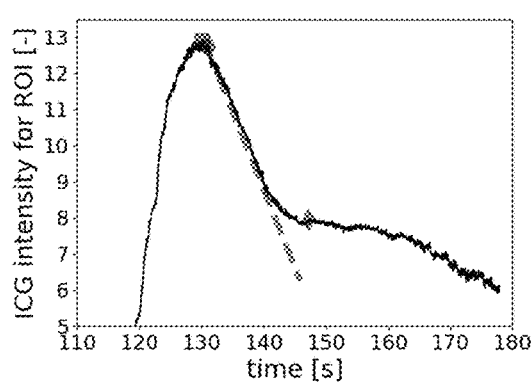

FIGS. 5A-5F show three examples illustrating the herein disclosed approach of analysing the washout of the fluorescence contrast agent. The intensity curves are the same as in FIG. 4. FIGS. 5B, 5D and 5F are close-ups of FIGS. 5A, 5C and 5E, respectively, where the ICG is washed out. In the graphs to the left the max intensities have been indicated by a star in FIG. 5A and by a square in FIGS. 5C and 5E. A close-up of the washout part is shown in the graphs to the right. The washout data has been analysed the same way as the perfusion slope and all possible washout slopes have been calculated. Similar to the above exemplified determination of the perfusion slope, the washout slopes can be binned and sorted in a histogram (not shown) in order to select the washout slope with the highest frequency. Washout start is typically after the max intensity of the curve. In this example washout starts are defined as being symmetric to the max slope intensity around the max curve intensity. Washout end is in this example determined the same way as the above exemplified determination of max slope intensity, i.e. when the intensity differs from the washout slope by a predefined constant times the standard deviation of the washout slope.

Figure 6A:
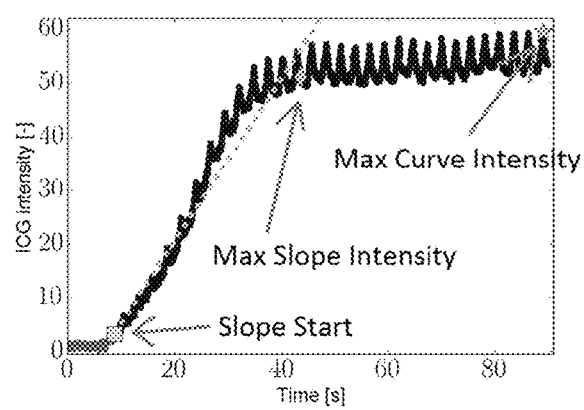
FIGS. 6A-6D show analysis of two additional fluorescence measurements using ICG illustrating the robustness of the presently disclosed analytical approach.
Figure 6B:
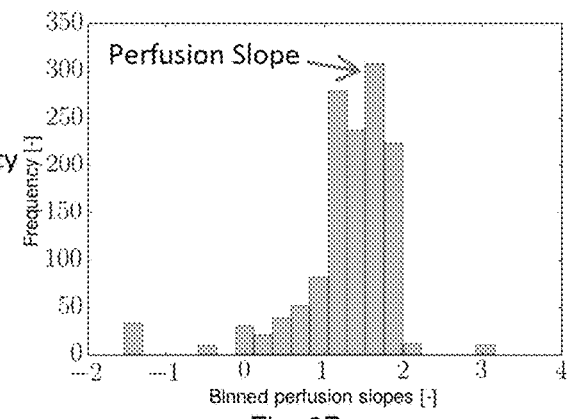

FIGS. 6A-6D show analysis of two additional fluorescence measurements using ICG illustrating the robustness of the presently disclosed analytical approach. The first in FIG. 6A shows the intensity data, slope start, the calculated perfusion slope (dotted line), max slope intensity and max curve intensity. The graph to the right shows the histogram with binned perfusion slope data. The intensity data is seen to be less stable than the other intensity curves disclosed herein with many local variations and no clear decrease in intensity after the perfusion slope. There will be a washout of the ICG molecules, but the data shown here do not include that part. FIGS. 6A and 6B illustrate that the exemplified approach disclosed herein is a very robust procedure that can be used for automatic and real-time determination of the perfusion slope and the other perfusion parameters derived therefrom. FIG. 6A also shows the large difference between the time points of the max slope intensity and the max curve intensity. The slope rise time derived from the max slope intensity is seen to be a much more relevant parameter to characterize the passage of the ICG bolus.

Figure 6C:
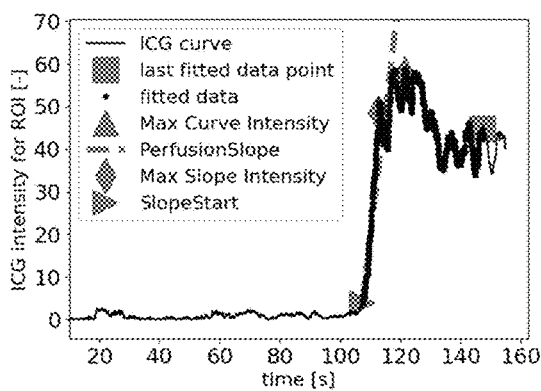
Figure 6D:
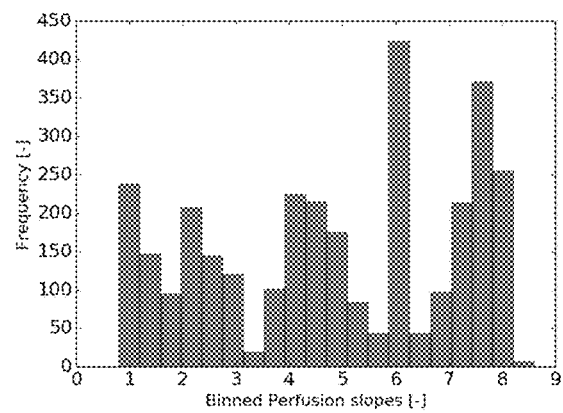

The second in FIG. 6C shows also unstable intensity data and all the calculated perfusion slopes are spread over a large interval as seen in the corresponding histogram in FIG. 6D. But by selecting the histogram bin with the highest frequency, relevant and precise perfusion slope parameters can nevertheless be extracted from the data, providing another example of the robustness of the presently disclosed approach.

Figure 7:
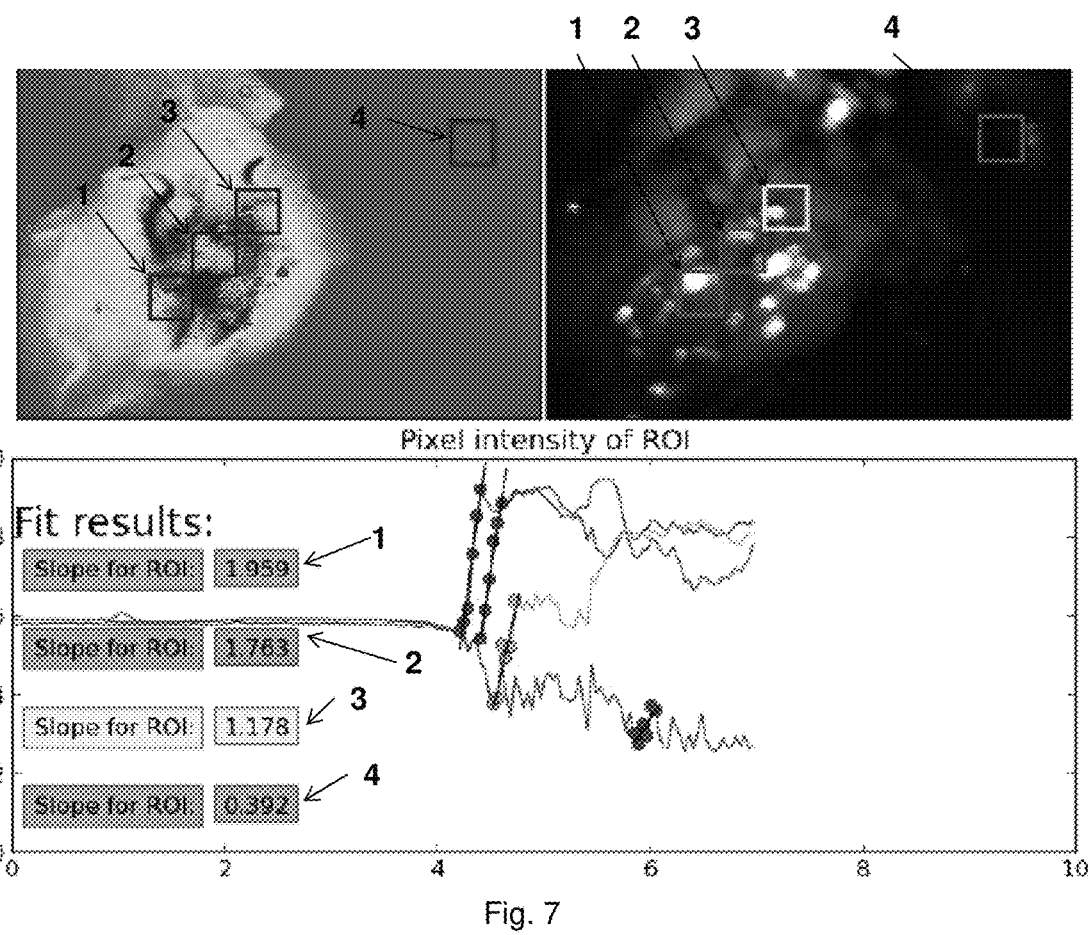
FIG. 7 shows an output video frame acquired during bowel surgery, four different regions of interest and analysis thereof.

FIG. 7 shows an output video frame from a video sequence acquired during bowel surgery. The upper right corner shows the raw footage (i.e. one frame) from the operation acquired during ICG bolus passage. The upper left corner shows the same video frame after image processing and the tissue perfusion is now much more clearly seen. As pointed out in the figures four regions of interest (1, 2, 3, 4) are indicated in the video frame. The graph below shows the mean pixel intensity of the four regions of interest plotted as a function of time (seconds) vs. normalized intensity. Perfusion slopes are calculated for the four ROIs (1, 2, 3, 4) and shown in the graph as straight lines.

When looking at only the two upper video frames, it is impossible for the surgeon to identify whether all of ROIs 1, 2 and 3, are equally and adequately perfused, e.g. whether the regions 1, 2 and 3 would be equally suited to place an anastomosis. This is also seen in the graph below after ~70 seconds, where the pixel intensities of ROI 1, 2 and 3 are similar. But by applying the herein disclosed approach of determining the perfusion slopes of the different ROIs, objective perfusion measures can be provided to the surgeon instantly. In the example in FIG. 7 it is seen from the calculated perfusion slopes, that there is reduced perfusion in ROI 3 compared to ROI 1 and ROI 2. This information provides the surgeon with objective perfusion parameters on which to base his surgical decisions and thereby ultimately increase the chance of a successful surgical outcome.

Figure 8A:
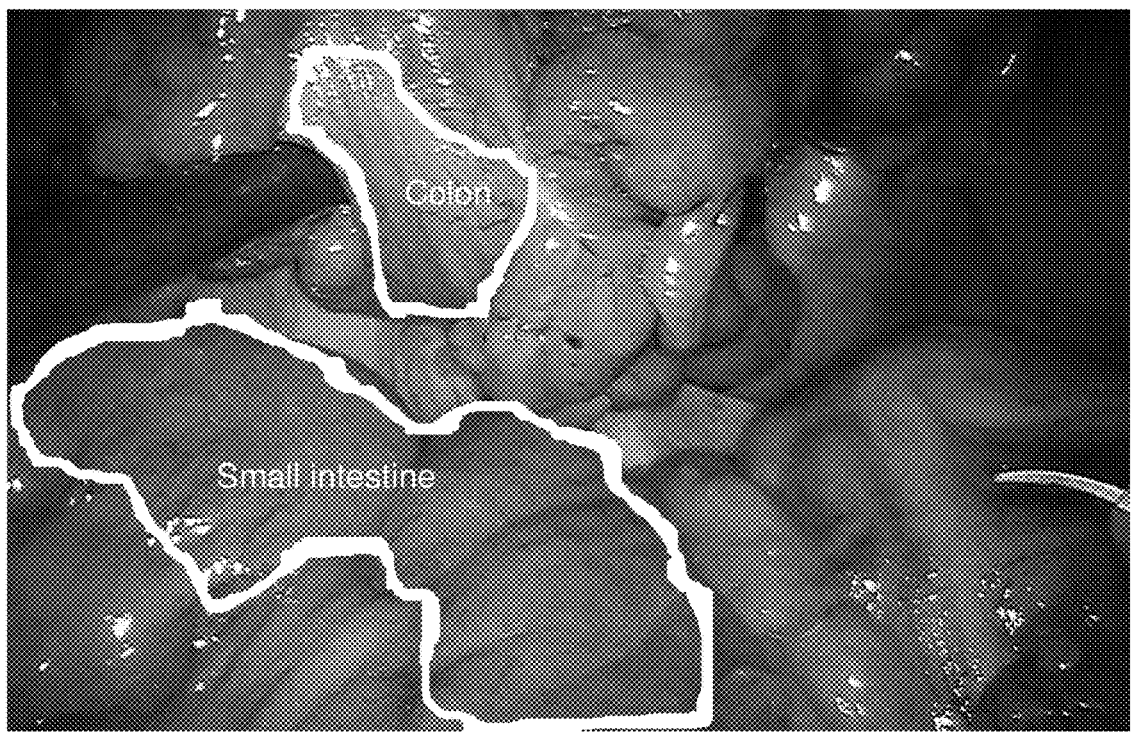
FIG. 8A shows a still image from a normal video sequence acquired before resection of the colon of a patient. The image shows the small intestine (lower part) and the colon (upper part).

FIG. 8A shows a still image from a normal video sequence acquired before resection of the bowel of a patient. The image shows the small intestine (lower part) and the colon (upper part). It is the colon which is about to be resected but by including the small intestine in the image analysis it is possible to provide an additional, possibly unbiased, high-perfusion reference measurement of the perfusion of the patient to be used for comparison with later perfusion measurements.

Figure 8B:
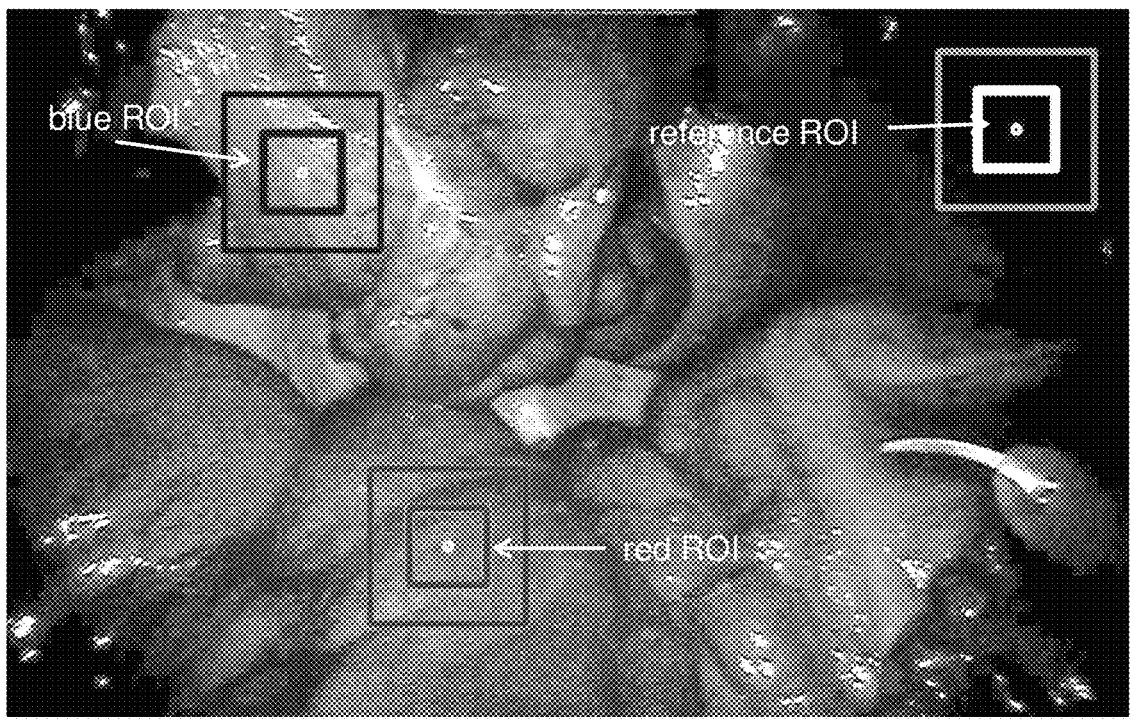
FIG. 8B shows a fluorescent image of substantially the same subsection of the gastrointestinal tract as in FIG. 8A but acquired later, i.e. after a bolus of a fluorescent contrast agent (ICQ) has been injected in the patient.

FIG. 8B shows a fluorescent image of substantially the same subsection of the gastrointestinal tract as in FIG. 8A but acquired later, i.e. after a bolus of a fluorescent contrast agent (ICG) has been injected in the patient. Three ROIs are indicated in the image to be used for image analysis: An upper left blue box located at the colon, a lower red box located at the small intestine (high-perfusion reference) and an upper right box located at a reference position in the image substantially without blood perfusion (no/low-perfusion reference).

Figure 9A:
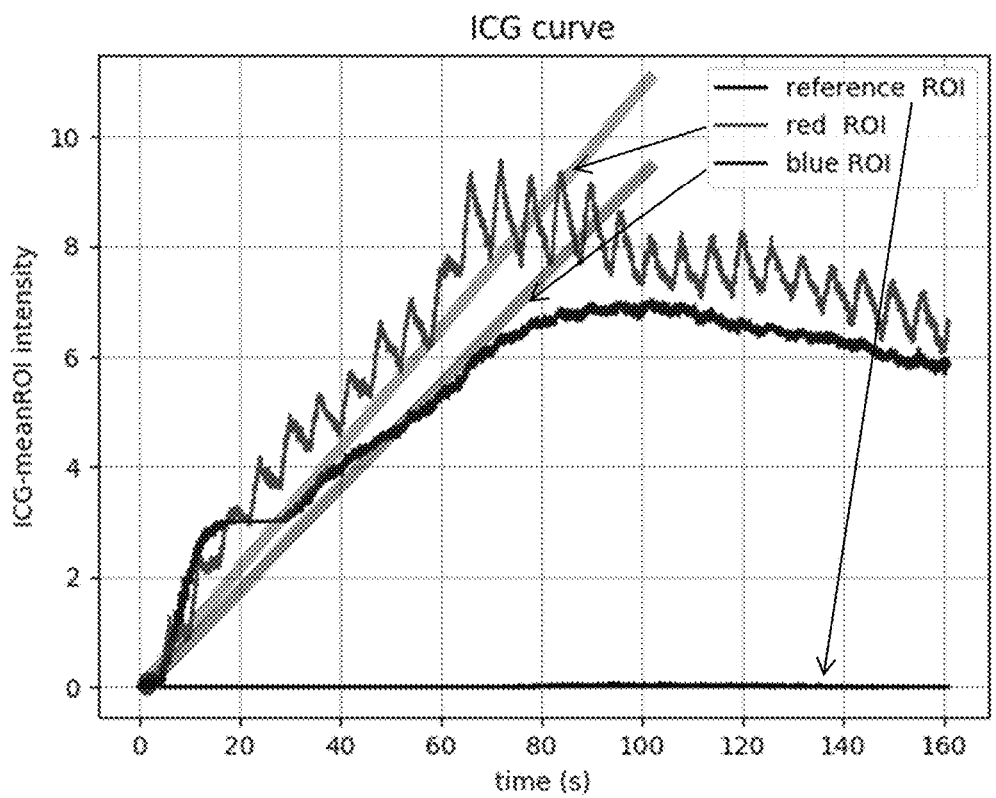
FIG. 9A shows the resulting intensity curves in the ROIs of FIG. 8B and the perfusion slopes calculated according to the herein disclosed approach, i.e. the perfusion slopes of the colon and the small intestine before resection.

FIG. 9A shows the resulting intensity curves in the ROIs of FIG. 8B and the perfusion slopes calculated according to the herein disclosed approach, i.e. the perfusion slopes of the colon and the small intestine before resection. Even though the intensity curves look quite different, the calculated perfusion slopes for the colon and the small intestine are comparable, however, with the perfusion slope of the small intestine being steeper than the perfusion slope of the colon (higher level of perfusion). This is also summarized in FIG. 9B where the perfusion slopes of the small intestine (left) and the colon (right) has been normalized relative to the perfusion slope of the small intestine.

Figure 10A:
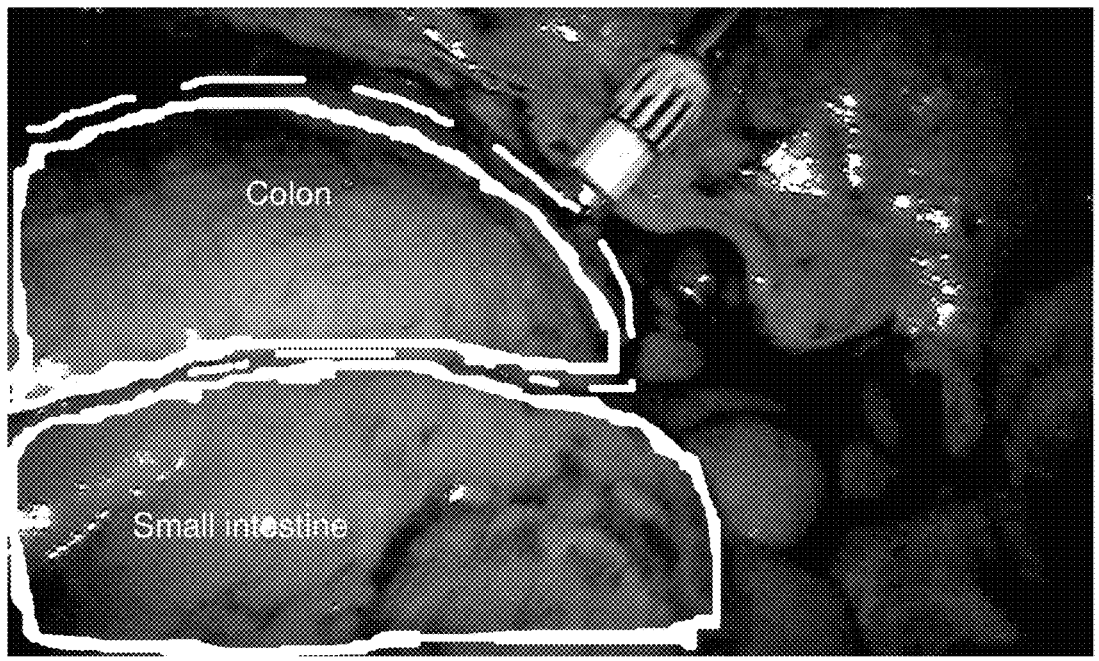
FIG. 10A shows a normal image of substantially the same subsection of the gastrointestinal tract as in FIG. 8A but acquired after resection of the colon—but before anastomosis.

FIG. 10A shows a normal image of substantially the same subsection of the gastrointestinal tract as in FIG. 8A but acquired after resection of the bowel—but before anastomosis. This is a crucial part of the operation where the surgeon must assess whether the perfusion of the two ends of bowel that are left after the resection is adequate for the anastomosis, or whether more of the bowel must be resected to ensure that the anastomosis is created in a region with optimal perfusion, ultimately increasing the chance of a successful outcome. The surgeon is therefore interested in obtaining a measure of the perfusion of various regions of the bowel around the resection. The small intestine is marked in the bottom of the image and the resected bowel (colon) is marked in the top of the image.

Figure 10B:
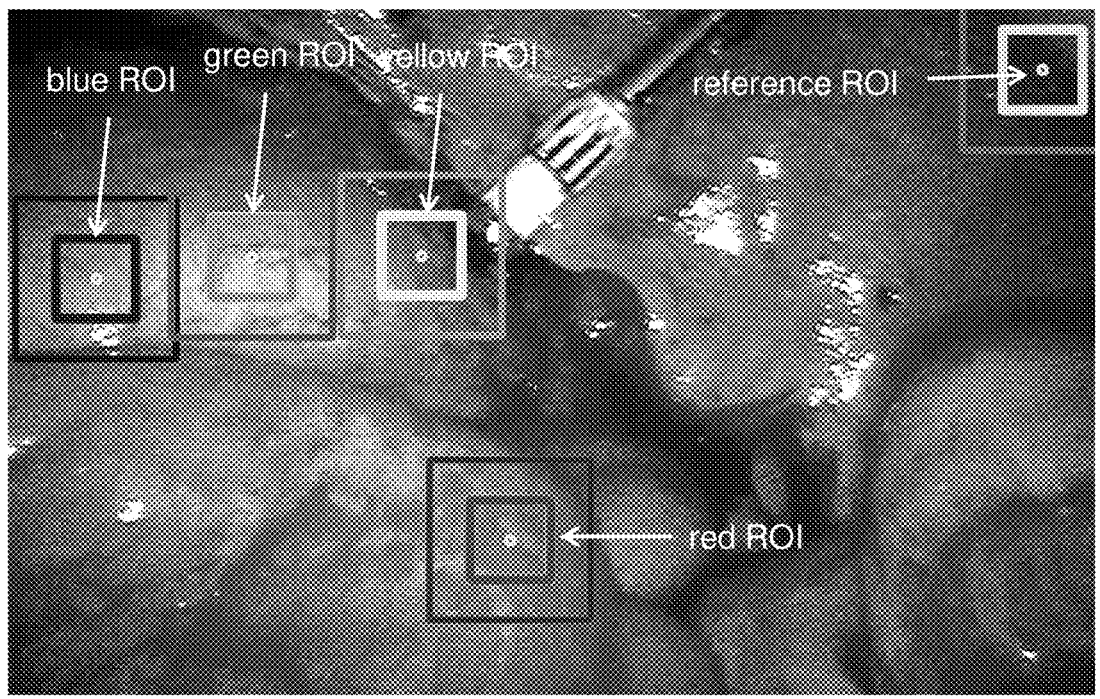
FIG. 10B is a fluorescent image which corresponds to the image in FIG. 10A after a bolus of ICG has been injected. Five ROIs are indicated in the image.

FIG. 10B is a fluorescent image which corresponds to the image in FIG. 10A after a bolus of ICG has been injected. Five ROIs are indicated in the image: One (red) on the small intestine as a high-perfusion reference, one (black) located at a reference position in the image substantially without blood perfusion (no/low-perfusion reference) and three (blue, green and yellow) on the resected bowel (colon).

Figure 9B:
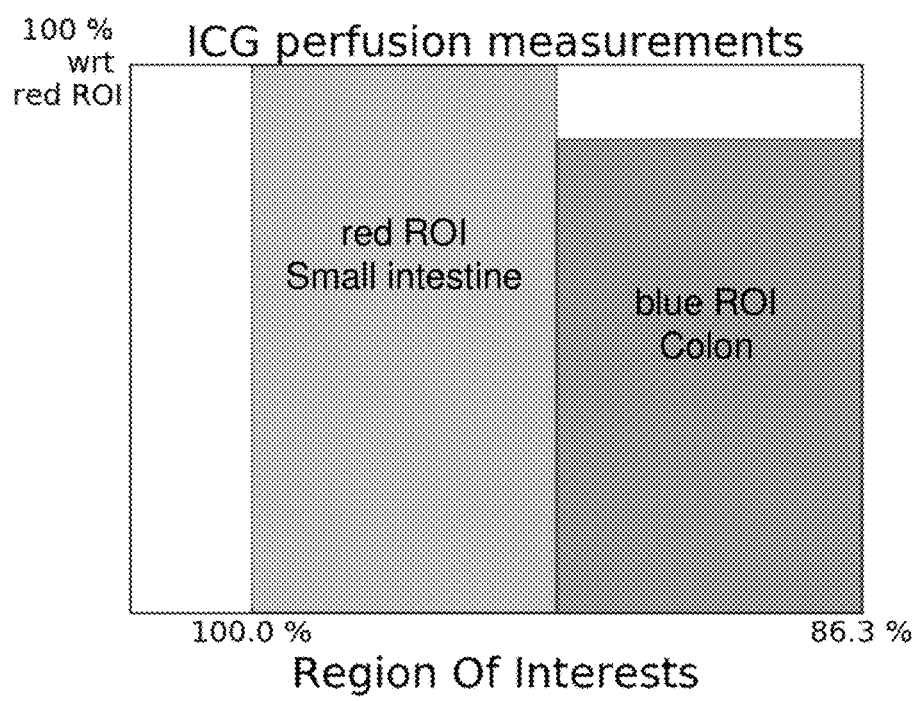
FIG. 9B shows the perfusion slopes of the small intestine (left) and the colon (right) from FIG. 9A, but here in FIG. 9B the slopes have been normalized relative to the perfusion slope of the small intestine.
Figure 11A:
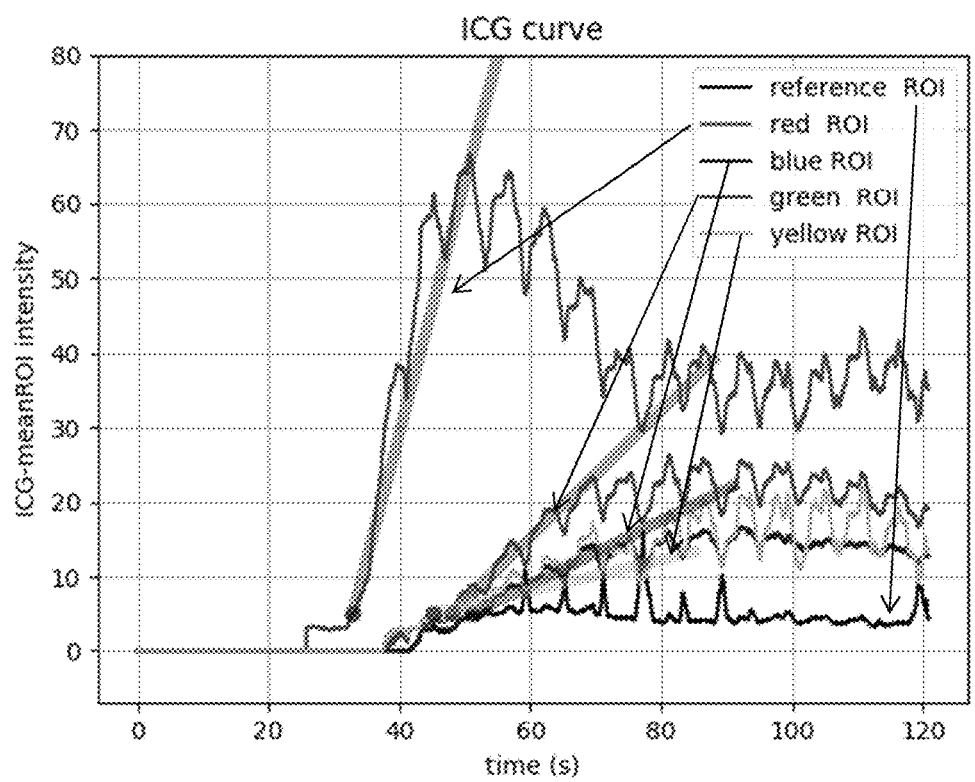
FIG. 11A shows the resulting intensity curves from the measurement illustrated in FIGS. 10A and 10B.
Figure 11B:
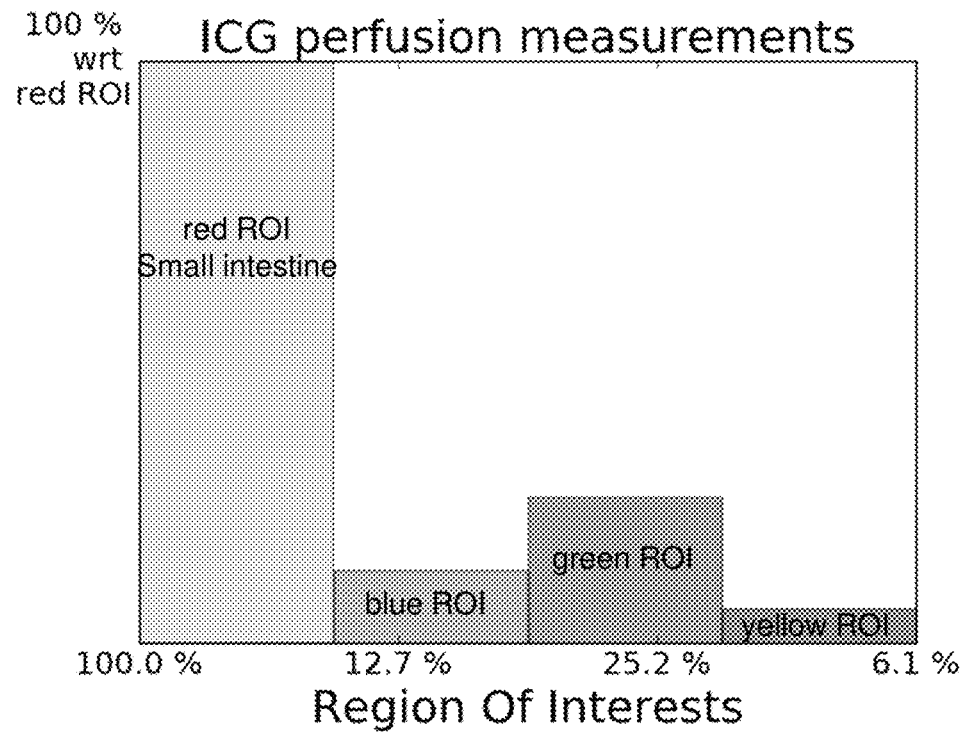
FIG. 11B shows the perfusion slopes of the small intestine (left) and the colon (blue, green and yellow to the right) from FIG. 11A, but here in FIG. 11B the slopes have been normalized relative to the perfusion slope of the small intestine.

FIG. 11A shows the resulting intensity curves from the measurement illustrated in FIGS. 10A and 10B. The red ROI corresponds to the small intestine giving the steepest perfusion slope and the black reference ROI naturally giving the lowest perfusion slope. The blue, green and yellow ROIs. corresponding to the three ROIs which were located on the bowel, provide comparable perfusion slopes, as also summarized in FIG. 11B where the perfusion slopes of the small intestine (left, red) and the bowel (blue, green and yellow to the right) has been normalized relative to the perfusion slope of the small intestine. Comparing to FIG. 9B there is a pronounced difference. In FIG. 9B (before resection) the perfusion in the bowel was comparable to the perfusion in the small intestine, whereas after resection the perfusion in the resected bowel is much lower than the small intestine. It is further noted that when comparing FIG. 9A (before resection) with FIG. 11A (after resection), the perfusion slope in absolute numbers is much larger after resection, also for the small intestine. This indicates that the absolute value of the perfusion slope (and the other perfusion parameters) is less important than a relative value as also demonstrated in FIGS. 9B and 11B. I.e. it is important to have one or more reference ROIs in the image analysis such that the calculated perfusion parameters can be compared to comparable perfusion parameters acquired from the same video footage. In this example, the herein disclosed approach of determining the perfusion detects a marked fall in perfusion of the bowel (colon) relative to the perfusion of the small intestines. This important information can guide the surgeon when choosing the optimal location of the anastomosis.

REFERENCES

[1] C. Toens et al: Validation of IC-VIEW fluorescence videography in a rabbit model of mesentereic ischaemia and reperfusion. Int J Colorectal Dis 2006; 21:332-338.
[2] N. Nerup et al: Quantification of fluorescence angiography in a porcine model. Langenbecks Arch Surg, published online Nov. 15, 2016.
[3] L. Boni et al: Indocyanine green-enhanced fluorescence to assess bowel perfusion during laparoscopic colorectal resection. Surg Endosc (2016) 30:2736-2742
[4] R. Uitert et al: A stable optic-flow based method for tracking colonoscopy images. Conference Paper, July 2008
[5] US 2016/262638
[6] D. Stein et al.: Colon Resection. http://emedicine.medscape.com/article/1891505-overview, September 2015

ITEMS

1. A (computer implemented) method for image processing hemodynamics in at least a part of an anatomical structure in video images acquired from a subject, comprising the steps of:
    performing image analysis of at least one video sequence acquired after a fluorescent contrast agent has been supplied to the subject,
    calculating intensity values in one or more regions of interest based on the image analysis, and
    determining the perfusion slope of the flow of the fluorescent contrast agent through at least one of said regions of interest.
2. The method according to item 1 wherein the anatomical structure is the gastrointestinal tract, preferably including buccal cavity; pharynx; the small intestine including duodenum, jejunum, and ileum; the stomach, including esophagus, cardia, and pylorus; the large intestine including cecum, colon, rectum and the anal canal.
3. A (computer implemented) method for image processing (mammalian) anastomosis hemodynamics (during a laparoscopic procedure involving the gastrointestinal tract) in video images acquired from a subject, comprising the steps of
    performing image analysis of at least the following two video sequences, each video sequence acquired after a fluorescent contrast agent has been supplied to the subject:
        i. first video images representing at least a first part of the gastrointestinal tract, and
        ii. second video images representing at least a second part of the gastrointestinal tract, the second part of the gastrointestinal tract being different than the first part of the gastrointestinal tract,
    calculating intensity values in one or more regions of interest based on the image analysis of the first video images and the second video images, and
    determining the perfusion slopes of the flow of the fluorescent contrast agent through at least a first region of interest selected in the first video sequence and at least a second region of interest selected in the second video sequence.
4. A (computer implemented) method for image processing (mammalian) anastomosis hemodynamics (during surgery involving the gastrointestinal tract) in video images acquired from a subject, comprising the steps of:
    performing image analysis of one, two or more of the following video sequences, each video sequence acquired after a fluorescent contrast agent has been supplied to the subject:
        a. video images representing at least a part of the gastrointestinal tract acquired before resection,
        b. video images representing at least a part of the gastrointestinal tract acquired after resection but before anastomosis, and
        c. video images representing at least a part of the gastrointestinal tract acquired after anastomosis
    calculating intensity values in one or more regions of interest based on the image analysis, and
    determining the perfusion slope of the flow of the fluorescent contrast agent through at least one of said regions of interest.
5. The method according to any of preceding items, wherein the perfusion slope is defined by the slope of said intensity values from slope start to slope end, wherein slope start is defined as the point in time where the slope exceeds a predefined first threshold.
6. The method according to any of preceding items 5, wherein the first threshold is determined by a predefined factor k and the mean and standard deviation (std) of intensity values prior to slope start and wherein slope start is defined as the time point where the slope exceeds the mean by k*std.
7. The method according to any of preceding items 5-6, wherein slope end is defined as the point in time, after slope start, where the slope is reduced by more than a predefined second threshold.
8. The method according to any of preceding items 5-7, wherein the perfusion slope is determined from a histogram in a parameter space binning all slope values calculated after slope start and based on the slope start value and where the perfusion slope is determined as the most frequent value of the histogram.

9. The method according to any of preceding items 5-8, wherein the slope values calculated immediately after slope start is assigned more weight in the histogram than later slope values.

10. The method according to any of preceding items, further comprising the step of determining the washout slope of the extinctive flow of the fluorescent contrast agent through at least one of said regions of interest.

11. The method according to any of preceding items 10, wherein the washout slope is defined by the slope of said intensity values from washout start to washout end, wherein washout start is after perfusion slope end.

12. The method according to any of preceding items 10-11, wherein the washout slope is determined from a histogram in a parameter space binning all calculated slope values after washout start and where the washout slope is determined as the most frequent value of the histogram.

13. The method according to any of preceding items, further comprising the step of determining the max slope intensity, defined as the intensity value at perfusion slope end.

14. The method according to any of preceding items, further comprising the step of determining the max slope intensity, defined as the intensity value at the time point where the distance to the perfusion slope exceeds a predefined limit, for example a limit based on a constant ($k_2$) times the standard deviation of the perfusion slope.

15. The method according to any of preceding items, further comprising the step of determining the slope rise time, defined as the difference between the time point of the max slope intensity and slope start.

16. The method according to any of preceding items, further comprising the step of determining the relative perfusion slope, defined as the inverse of the slope rise time.

17. The method according to any of preceding items, further comprising the step of determining the subject specific relative perfusion slope, defined as the relative perfusion slope times an extrema intensity of a separate, preferably subject specific, region of interest.

18. The method according to any of preceding items 3-17, further comprising the step of
performing image analysis of at least the following two video sequences, each video sequence acquired after a fluorescent contrast agent has been supplied to the subject:
first video images representing at least a first part of the gastrointestinal tract, and
second video images representing at least a second part of the gastrointestinal tract, the second part of the gastrointestinal tract being different than the first part of the gastrointestinal tract,
calculating intensity values in one or more regions of interest based on the image analysis of the first video images and the second video images, and
determining the perfusion slopes of the flow of the fluorescent contrast agent through at least a first region of interest selected in the first video sequence and at least a second region of interest selected in the second video sequence.

19. The method according to any of preceding items 3-17, further comprising the step of
performing image analysis of two or more of the following video sequences, each video sequence acquired after a fluorescent contrast agent has been supplied to the subject:
video images representing at least a part of the gastrointestinal tract acquired before resection,
video images representing at least a part of the gastrointestinal tract acquired after resection but before anastomosis, and
video images representing at least a part of the gastrointestinal tract acquired after anastomosis
calculating intensity values in one or more regions of interest based on the image analysis, wherein at least a first of said regions of interest is the same region in said two or more video sequences, and
determining the perfusion slopes of the flow of the fluorescent contrast agent through at least the first region of interest based on said two or more video sequences.

20. The method according to any of preceding items 18-19, further comprising the step of determining one or more of the following parameters based on said two or more video sequences: the washout slopes, the max slope intensities, the relative perfusion slopes and the subject specific relative perfusion slopes.

21. The method according to any of preceding items 18-20, further comprising the step of calculating quantitative data for the perfusion in at least one of said regions of interest based on slope parameters determined from said at least two video sequences.

22. The method according to any of preceding items, further comprising the step of selecting one or more regions of interest in at least one of said video images, at least a first of said regions of interest corresponding to a subsection of the gastrointestinal tract.

23. The method according to any of preceding items, further comprising the step of tracking movements of at least a part of the gastrointestinal tract in said video images, and correlating said movements such that at least said first region of interest corresponds to the same subsection of the gastrointestinal tract in said video images.

24. The method according to any of preceding items, wherein the video images are acquired before, during and/or after laparoscopic surgery.

25. A (computer implemented) method for image processing movements/dynamics of at least a part of the gastrointestinal tract, such as during surgery, from video images representing at least said part of the gastrointestinal tract, comprising the steps of:
selecting one or more regions of interest in at least one of said video images, at least a first of said regions of interest corresponding to a subsection of the gastrointestinal tract,
tracking movements of the gastrointestinal tract in said video images, and
correlating said movements such that at least said first region of interest corresponds to the same subsection of the gastrointestinal tract in said video images.

26. The method according to any of preceding items 23-25, wherein movement tracking is provided by free image tracking.

27. The method according to any of preceding items 23-25, wherein movement tracking is provided by free image tracking in the form of classifier based tracking comprising the step of determining classifiers of one more recognizable features in the video images, preferably in an area adjacent or surrounding at least one of the regions of interest.

28. The method according to any of preceding items 23-25, wherein movement tracking is provided by free image tracking in the form of colour based tracking.

29. The method according to any of preceding items 28, wherein movement tracking is based on colour tracking of one or more colour markers which have been applied on to the gastrointestinal tract.
30. The method according to any of preceding items 28-29, wherein movement tracking comprises the step of colour filtering and thresholding to obtain a Boolean map of pixels in the video images.
31. The method according to any of preceding items 30, further comprising the step of noise filtering to improve the Boolean map.
32. The method according to any of preceding items 23-25, wherein movement tracking is provided by object based tracking.
33. The method according to any of preceding items 32, wherein movement tracking is provided by tracking the movement of one or more predefined objects attached to the gastrointestinal tract.
34. The method according to any of preceding items, wherein the video sequence(s) represent an exterior portion of the gastrointestinal tract, such as a part of the gastrointestinal wall, such as a portion of the external tissue of the gastrointestinal tract.
35. The method according to any of preceding items, wherein at least one of said regions of interest covers a section of an exterior portion of the gastrointestinal tract.
36. The method according to any of preceding items, wherein at least one of said regions of interest covers a section which is not the gastrointestinal tract.
37. The method according to any of preceding items, wherein the fluorescent contrast agent is selected from the group of: indocyanin green (ICG) and fluorescin.
38. The method according to any of preceding items, wherein the video sequences are acquired using natural light or infrared light or a combination thereof.
39. A system for measuring and/or assessing hemodynamics in an anatomical structure of a subject comprising
an imaging device for acquiring video images of the exterior portion of at least a part of said anatomical structure, such as the gastrointestinal tract and
an image processing device configured for carrying out the method of any of the preceding items 1-37.
40. A system for measuring and/or assessing hemodynamics in an anatomical structure of a subject, comprising a non-transitive, computer-readable storage device for storing instructions that, when executed by a processor, performs a method according to any of items 1-37.
41. An electroat leastnic medical device comprising a processor and a memory and being adapted to perform the method measuring and/or assessing hemodynamics in an anatomical structure of a subject according to any items 1-37.
42. A computer program having instructions which when executed by a computing device or system causes the computing device or system to measure and/or assess hemodynamics in an anatomical structure of a subject according to any of items 1-37.

The invention claimed is:
1. A method for assessing hemodynamics in at least a first part of the gastrointestinal tract in video images acquired from a subject, the method comprising the steps of: supplying a fluorescent contrast agent to the subject,
acquiring at least one first video sequence of at least said first part of the gastrointestinal tract after said fluorescent contrast agent has been supplied to the subject,
performing image analysis of at least a part of said first video sequence thereby calculating intensity values in at least one region of interest selected in the analysed video sequence, and
determining a perfusion slope of the flow of the fluorescent contrast agent through at least one of said regions of interest,
wherein the perfusion slope is defined by the slope of said intensity values from a slope start, wherein the slope start is defined as a point in time where a slope of said intensity values exceeds a predefined first threshold and wherein the perfusion slope is determined from a histogram wherein all slope values calculated after said slope start are divided by value into bins that are a series of consecutive, adjacent, and non-overlapping intervals, and wherein the slope values in the histogram are assigned a weight based on a distance to the slope start, such that slope values calculated after the slope start at a relative distance closer to the slope start are assigned a greater weight in the histogram than the slope values calculated after the slope start at a relative distance farther from the slope start, such that the perfusion slope is selected from the histogram based on weight of each slope value and number of slope values in each bin, and
wherein the perfusion slope is a direct indication of blood flow in superficial tissue of at least the first part of the gastrointestinal tract.
2. The method according to claim 1, wherein the first threshold is determined by a predefined factor k and the mean and standard deviation (std) of intensity values prior to slope start and wherein slope start is defined as the time point where the slope exceeds the mean by k*std.
3. The method according to claim 1, further comprising the step of determining the washout slope of the extinctive flow of the fluorescent contrast agent through at least one of said regions of interest, wherein the washout slope is defined by the slope of said intensity values from washout start to washout end, wherein washout start is after perfusion slope end and wherein the washout slope is determined from a histogram in a parameter space binning all calculated slope values after washout start and where the washout slope is determined as the most frequent value of the histogram.
4. The method according to claim 1, further comprising the step of determining the max slope intensity, defined as the intensity value at the time point where the distance to the perfusion slope exceeds a predefined limit.
5. The method according to claim 1, further comprising the step of 1) determining the slope rise time, defined as the difference between the time point of the max slope intensity and slope start, and 2) determining the relative perfusion slope, defined as the inverse of the slope rise time.
6. The method according to claim 5, further comprising the step of determining the subject specific relative perfusion slope, defined as the relative perfusion slope times an extrema intensity of a separate region of interest.
7. The method according to claim 1, further comprising the step of determining at least a second of the following parameters: the perfusion slope, the washout slope, the max slope intensity, the relative perfusion slope and the subject specific relative perfusion slope of the flow of the fluorescent contrast agent through at least a second of said regions of interest, wherein the first and second regions of interest represent different parts of the gastrointestinal tract.
8. The method according to claim 7, wherein said different parts are the colon and the small intestine.

9. The method according to claim 1, further comprising the steps of
performing image analysis of two or more of the following video sequences, each video sequence acquired after a fluorescent contrast agent has been supplied to the subject:
video images representing at least a part of the gastrointestinal tract acquired before resection,
video images representing at least a part of the gastrointestinal tract acquired after resection but before anastomosis, and
video images representing at least a part of the gastrointestinal tract acquired after anastomosis
calculating intensity values in one or more regions of interest based on the image analysis, wherein at least a first of said regions of interest is the same region in said two or more video sequences, and
determining the perfusion slopes of the flow of the fluorescent contrast agent through at least the first region of interest based on said two or more video sequences.

10. The method according to claim 9, further comprising the steps of 1) determining one or more of the following parameters based on said two or more video sequences: the washout slopes, the max slope intensities, the relative perfusion slopes and the subject specific relative perfusion slopes, and 2) calculating quantitative data for the perfusion in at least one of said regions of interest based on slope parameters determined from said at least two video sequences.

11. The method according to claim 9, wherein a new resection is provided if the determined perfusion after resection of the gastrointestinal tract has dropped below a predefined critical value compared to the perfusion determined before resection.

12. The method according to claim 1, further comprising the step of tracking movements of at least a part of the gastrointestinal tract in said video images, and correlating said movements such that at least said first region of interest corresponds to the same subsection of the gastrointestinal tract in said video images.

13. The method according to claim 12, wherein movement tracking is provided by free image tracking in the form of classifier based tracking comprising the step of determining classifiers of one or more recognizable features in the video images.

14. The method according to claim 13, wherein the classifiers are determined in an area adjacent or surrounding at least one of the regions of interest.

15. The method according to claim 12, wherein movement tracking is provided by free image tracking in the form of colour based tracking based on 1) colour tracking of one or more colour markers which have been applied on to the gastrointestinal tract, or 2) colour filtering and thresholding to obtain a Boolean map of pixels in the video images.

16. The method according to claim 12, wherein movement tracking is provided by object based tracking based in tracking the movement of one or more predefined objects attached to the gastrointestinal tract.

17. The method according to claim 1, wherein said part of the gastrointestinal tract is selected from the group of: buccal cavity; pharynx; the small intestine including duodenum, jejunum, and ileum; the stomach, including esophagus, cardia, and pylorus; the large intestine including cecum, colon, rectum and the anal canal.

18. The method according to claim 1, wherein the video sequences are acquired using natural light or infrared light or a combination thereof.

19. A system for measuring and/or assessing hemodynamics in at least a first part of the gastrointestinal tract of a subject,
an imaging device for acquiring at least one first video sequence of the exterior portion of at least said first part of the gastrointestinal tract after a fluorescent contrast agent has been supplied to the subject,
a computer configured for performing image analysis of at least a part of said first video sequence thereby
calculating intensity values in at least one region of interest selected in the analysed video sequence, and
determining the perfusion slope of the flow of the fluorescent contrast agent through at least one of said regions of interest,
wherein the perfusion slope is defined by the slope of said intensity values from a slope start, wherein the slope start is defined as a point in time where a slope of said intensity values exceeds a predefined first threshold and wherein the perfusion slope is determined from a histogram wherein all slope values calculated after said slope start are divided by value into bins that are a series of consecutive, adjacent, and non-overlapping intervals, and wherein the slope values in the histogram are assigned a weight based on a distance to the slope start, such that slope values calculated after the slope start at a relative distance closer to the slope start are assigned a greater weight in the histogram than the slope values calculated after the slope start at a relative distance farther from the slope start, such that the perfusion slope is selected from the histogram based on weight of each slope value and number of slope values in each bin, and
wherein the perfusion slope is a direct indication of blood flow in superficial tissue of at least the first part of the gastrointestinal tract.

20. The method according to claim 4, wherein the predefined limit is a limit based on a constant (k2) times the standard deviation of the perfusion slope.

21. The method according to claim 1, wherein the perfusion slope is a direct indication of blood flow in tissue indicated in the video images.

* * * * *

UNITED STATES PATENT AND TRADEMARK OFFICE
CERTIFICATE OF CORRECTION

PATENT NO. : 10,271,750 B2
APPLICATION NO. : 15/838071
DATED : April 30, 2019
INVENTOR(S) : Madsen et al.

Page 1 of 1

It is certified that error appears in the above-identified patent and that said Letters Patent is hereby corrected as shown below:

On the Title Page

Item (12), United States Patent, Line 2, delete "Maden et al." and insert --Madsen et al.--, therefor.

Item (72), Inventors, delete "Mads Holst Aagaard Maden" and insert --Mads Holst Aagaard Madsen--, therefor.

Signed and Sealed this
Twenty-second Day of October, 2019

Andrei Iancu
*Director of the United States Patent and Trademark Office*